US 9,341,635 B2

(12) United States Patent
Baumann et al.

(10) Patent No.: US 9,341,635 B2
(45) Date of Patent: May 17, 2016

(54) MASS LABELS

(75) Inventors: Christian Baumann, Darmstadt (DE); Stefan Kienle, Frankfurt am Main (DE); Karsten Kuhn, Frankfurt am Main (DE); Harald Legner, Frankfurt am Main (DE)

(73) Assignee: ELECTROPHORETICS LIMITED, Cobham Surrey (GB)

( * ) Notice: Subject to any disclaimer, the term of this patent is extended or adjusted under 35 U.S.C. 154(b) by 0 days.

(21) Appl. No.: 13/497,875

(22) PCT Filed: Sep. 8, 2010

(86) PCT No.: PCT/EP2010/063191
§ 371 (c)(1),
(2), (4) Date: Jul. 23, 2012

(87) PCT Pub. No.: WO2011/036059
PCT Pub. Date: Mar. 31, 2011

(65) Prior Publication Data
US 2012/0283137 A1 Nov. 8, 2012

(30) Foreign Application Priority Data
Sep. 25, 2009 (GB) .................................. 0916881.6

(51) Int. Cl.
*C40B 30/10* (2006.01)
*C40B 40/04* (2006.01)
*C07D 401/12* (2006.01)
*G01N 33/74* (2006.01)
*C07B 59/00* (2006.01)
*C07D 211/14* (2006.01)
*G01N 33/58* (2006.01)

(52) U.S. Cl.
CPC ............ *G01N 33/743* (2013.01); *C07B 59/002* (2013.01); *C07D 211/14* (2013.01); *C07D 401/12* (2013.01); *G01N 33/58* (2013.01); *G01N 2458/15* (2013.01); *G01N 2560/00* (2013.01); *Y10T 436/196666* (2015.01); *Y10T 436/200833* (2015.01); *Y10T 436/24* (2015.01)

(58) Field of Classification Search
CPC .............................. C07D 401/12; C40B 30/10
USPC .......................................................... 506/12
See application file for complete search history.

(56) References Cited

U.S. PATENT DOCUMENTS

| 2,324,283 | A | | 7/1943 | D'Alelio | |
| 5,880,270 | A | * | 3/1999 | Berninger et al. | ......... 530/391.9 |
| 7,294,456 | B2 | | 11/2007 | Schmidt et al. | |
| 2003/0077616 | A1 | * | 4/2003 | Lomas | .............. 435/6 |
| 2005/0233399 | A1 | * | 10/2005 | Aebersold et al. | ........... 435/7.92 |
| 2011/0003395 | A1 | * | 1/2011 | Dey et al. | ........................ 436/98 |

FOREIGN PATENT DOCUMENTS

| EP | 1105517 B1 | 6/2001 |
| WO | 00/02895 A1 | 1/2000 |
| WO | 02/067684 A1 | 9/2002 |
| WO | 2004070352 A2 | 8/2004 |
| WO | 2007/012849 A2 | 2/2007 |
| WO | WO 2007012849 A2 * | 2/2007 |
| WO | 2007/031717 A1 | 3/2007 |
| WO | WO 2009141310 A1 * | 11/2009 |

OTHER PUBLICATIONS

Wong et al., Mitochondrial Protein Targets of Thiol-Reactive Electrophiles, Chem. Res. Toxicol., 2008, 21, 796-804.*
Thompson et al.; Tandem Mass Tags: A Novel Quantification Strategy for Comparative Analysis of Complex Protein Mixtures by MS/MS, Anal. Chem., 2003, 75, 1895-1904.*
Han et al.; Mass Spectrometry for Proteomics, NIH Author Manuscript, 2008, I-13; published in Curr Opin Chem Biol, 2008, 12(5), 483-490.*
Bantscheff et al., Quantitative Mass Spectrometry in Proteomics: A Critical Review, Anal Bioanal Chem, 2007, 389, 1017-1031.*
Diederen, Jeroen, International Search Report, PCT/EP2010/063191, European Patent Office, Feb. 18, 2011.
Gygi et al., "Quantitative Analysis of Complex Protein Mixtures Using Isotope-Coded Affinity Tags", Nature Biotechnology, Oct. 1999, pp. 994-999, vol. 17.

(Continued)

*Primary Examiner* — Maria Leavitt
*Assistant Examiner* — Amy M Bunker
(74) *Attorney, Agent, or Firm* — Arent Fox LLP

(57) ABSTRACT

A reactive mass label for labelling a biological molecule for detection by mass spectrometry, which label comprises a reactive functionality for labelling thiol groups or carbonyl groups. Also provided is a reactive mass label for labelling a biological molecule for detection by mass spectrometry, wherein the mass label comprises the following structure:

$$X\text{-}L\text{-}M\text{-}S\text{-}Re$$

wherein X is a mass marker moiety, L is a cleavable linker, M is a mass normalization moiety, S is a mass series modifying group comprising the following group:

$$\left[\underset{H}{N}\diagdown\diagup\underset{K}{\overset{J}{\diagdown}}\diagdown\underset{\underset{O}{\parallel}}{(CH_2)_n}\right]_m$$

wherein J is C=O, K is NH, and n is 2 or J and K are both $CH_2$ and n is 1, and wherein m is at least 1; and Re is a reactive functionality for attaching the mass label to a biological molecule.

5 Claims, 21 Drawing Sheets

(56) References Cited

OTHER PUBLICATIONS

Maskos et al., "Oligonucleotide hybridisations on glass supports: a novel linker for oligonucleotide synthesis and hybridisation properties of oligonucleotides synthesised in situ", Nucleic Acids Research, Mar. 1992, pp. 1679-1684, vol. 20.

Lloyd-Williams et. al., "Convergent Solid-Phase Peptide Synthesis", Tetrahedron, 1993, pp. 11065-11133, vol. 49.

Geahlen et. al., "A General Method for Preparation of Peptide's Biotinylated at the Carboxy Terminus", Analytical Biochemistry, 1992, pp. 68-70, vol. 202(1).

Sawutz et al., "Synthesis and Molecular Characterization of a Biotinylated Analog of [Lys]Bradykinin", Peptides, 1991, pp. 1019-1024, vol. 12(5).

Natarajan et al., "Site-Specific Biotinylation; A Novel Approach and its Application to Endothelin-1 Analogs and PTH-Analog", Int. J. Peptide Protein Res., 1992, pp. 567-574, vol. 40(6).

Schlosser et al., "Five-Membered Ring Formation in Unimolecular Reactions of Peptides: A Key Structural Element Controlling Low-Energy Collision-Induced Dissociation of Peptides", Journal of Mass Spectrometry, 2000, pp. 1382-1390, vol, 35.

\* cited by examiner

A

B

C

FIGURE 9
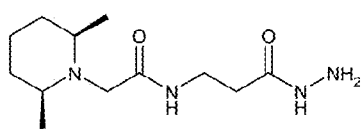
Figure 9(A)
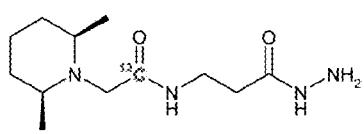     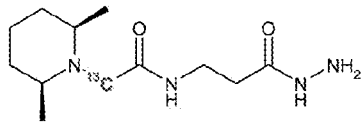
Figure 9(B)
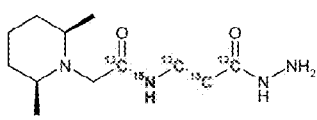     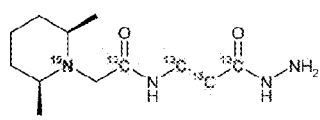     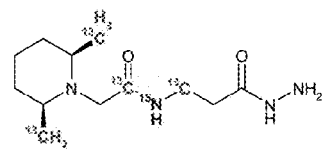
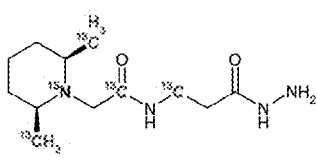     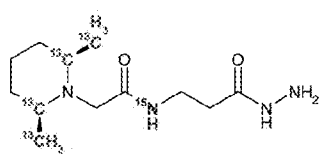     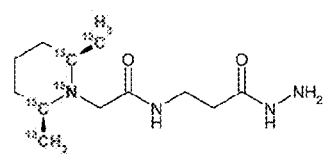
Figure 9(C)

FIGURE 10
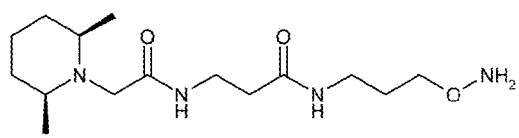
FIGURE 10(A)
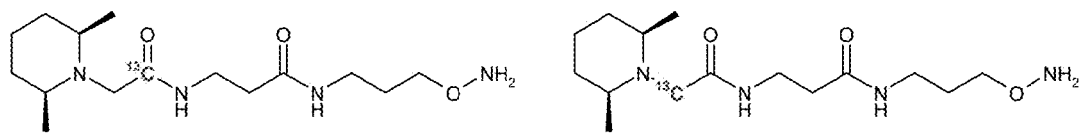
FIGURE 10(B)
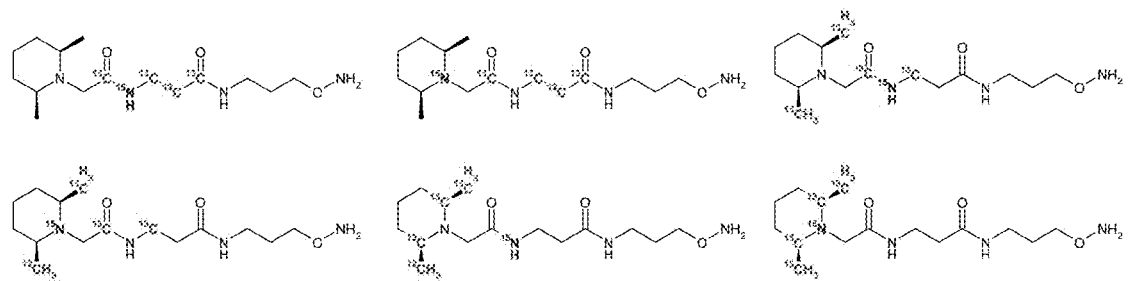
FIGURE 10(C)

Light-extended variant

Medium-extended variant (Δamu +4)

Heavy-extended variant (Δamu +4)

Light-extended variant

Heavy-extended variant (Δamu +6)

A
BSA, tryptic digested labelled with:

B

A)

B)

Cys-TMT⁶-126

Cys-TMT⁶-127

Cys-TMT⁶-128

Cys-TMT⁶-129

Cys-TMT⁶-130

Cys-TMT⁶-131

FIGURE 18
FIGURE 18(A)
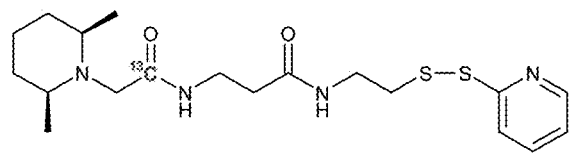
Cys-TMT²-126
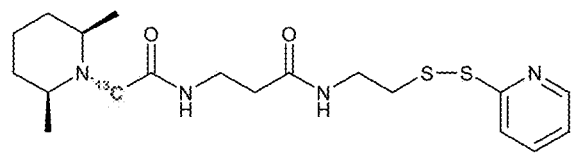
Cys-TMT²-127
FIGURE 18(B)
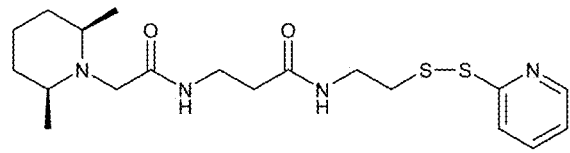
Cys-TMTzero FIGURE 19
FIGURE 19(A)
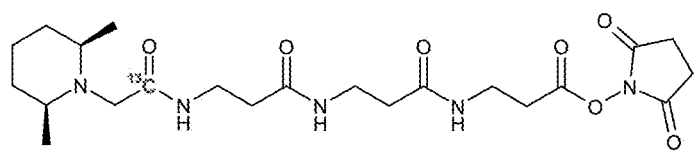
TMT²-126-2BA_light
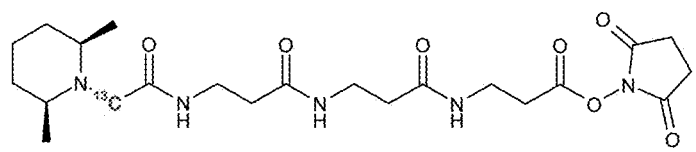
TMT²-127-2BA_light
FIGURE 19(B)
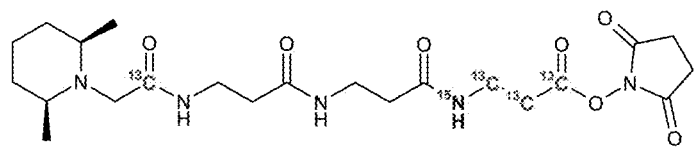
TMT²-126-2BA_medium
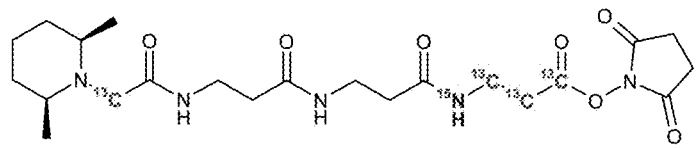
TMT²-127-2BA_medium

TMT²-126-2BA_heavy

TMT²-127-2BA_heavy

TMTzero-2BA_light

TMTzero-Ahx_light

MASS LABELS

CROSS REFERENCE TO RELATED APPLICATIONS

This application is a U.S. National Stage Application filed under 35 U.S.C. §371 and claims priority to International Application No. PCT/EP2010/063191, filed Sep. 8, 2010, which application claims priority to Great Britain Application No. 0916881.6, filed on Sep. 25, 2009, the disclosures of which are incorporated herein by reference.

FIELD OF THE INVENTION

This invention relates to compounds for labelling analytes, particularly biomolecules such as proteins. This invention also relates to methods of analysis by mass spectrometry, using specific mass labels.

BACKGROUND TO THE INVENTION

The field of human medicine has been dependent on the ability to detect changes caused by or in response to disease. Such changes provide means of diagnosis and offer insights to the targets for therapeutic compounds such as vaccines and medicines. A wide range of biological molecules can be used in medicine including nucleic acids, proteins, steroids, sugars and lipids. In this context, the ability to quantitatively detect such biomolecules using mass spectrometers has provided considerable advances in their study and application to human and veterinary disease, in environmental analysis and monitoring, and in food and beverage manufacturing. In particular the use of stable isotopes to provide synthetic quantitative references has been developed in isotope dilution mass spectrometry for monitoring of all classes of biomolecules. However, these methods have traditionally required an available synthetic standard which is not always possible.

Recently a range of chemical mass tags bearing heavy isotope substitutions have been developed to further improve the quantitative analysis of biomolecules by mass spectrometry. Depending on the tag design, members of tag sets are either isochemic having the same chemical structure but different absolute masses, or isobaric having both identical structure and absolute mass. Isochemic tags are typically used for quantitation in MS mode whilst isobaric tags must be fragmented in MS/MS mode to release reporter fragments with a unique mass. To date the isotopically doped mass tags have primarily been employed for the analysis of proteins and nucleic acids.

An early example of isochemic mass tags were the Isotope-Coded Affinity Tags (ICAT) (Gygi et al., Nature Biotechnology 17: 994-999, "Quantitative analysis of complex protein mixtures using isotope-coded affinity tags" 1999). The ICAT reagents are a pair of mass tags bearing a differential incorporation of heavy isotopes in one (heavy) tag with no substitutions in the other (light) tag. Two samples are labelled with either the heavy or light tag and then mixed prior to analysis by LC-MS. A peptide present in both samples will give a pair of precursor ions with masses differing in proportion to the number of heavy isotope atomic substitutions. Further examples of isochemic tags include the ICPL reagents that provide up to four different reagents.

Whilst isochemic tags allow a degree of improvement in the reproducibility of proteomic studies, this is achieved at the cost of increasing the complexity of the mass spectrum. To overcome this limitation, and to take advantage of greater specificity of tandem mass spectrometry the isobaric mass tags were developed. Since their introduction in 2000 isobaric mass tags have provided improved means of proteomic expression profiling by universal labelling of amine functions in proteins and peptides prior to mixing and simultaneous analysis of multiple samples. Because the tags are isobaric, having the same mass, they do not increase the complexity of the mass spectrum since all precursors of the same peptide will appear at exactly the same point in the chromatographic separation and have the same aggregate mass. Only when the molecules are fragmented prior to tandem mass spectrometry are unique mass reporters released, thereby allowing the relative or absolute amount of the peptide present in each of the original samples to be calculated.

U.S. Pat. No. 7,294,456 sets out the underlying principles of isobaric mass tags and provides specific examples of suitable tags wherein different specific atoms within the molecules are substituted with heavy isotope forms including 13C and 15N respectively. U.S. Pat. No. 7,294,456 further describes the use of offset masses to make multiple isobaric sets to increase the overall plexing rates available without unduly increasing the size of the individual tags. WO 2004/070352 describes additional sets of isobaric mass tags. WO 2007/012849 describes further sets of isobaric mass tags including 3-[2-(2,6-Dimethyl-piperidin-1-yl)-acetylamino]-propanoic acid-(2,5-dioxo-pyrrolidine-1-yl)-ester (DMPip-βAla-OSu).

Despite the significant benefits of previously disclosed isobaric mass tags there remains a need for further improvement both in the range of molecules that can be labelled with such tags, and also in the levels of multiplex analysis achievable. Accordingly, it is an aim of the present invention to provide a range of novel isobaric mass tags that specifically address the limitations of previously disclosed molecules.

STATEMENT OF INVENTION

The inventors found that by using a common core structure, preferably based on DMPip-βAla it was possible to develop a range of products with selective labelling properties and/or additional offset masses which circumvent the need to re-design workflows or software for interpretation of quantitative mass spectrometry data. In addition, they have shown that it is possible to use the same core structure to develop isochemic tags offering the benefit of quantitation in LC-MS with direct conversion to equivalent isobaric mass tags for biomarker qualification and/or clinical assay development.

Accordingly, the present invention provides a reactive mass label for labelling a biological molecule for detection by mass spectrometry, which label comprises the following structure:

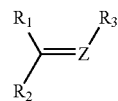

wherein $R_1$, $R_2$, $R_3$ and Z are selected from one of the following definitions a) to d):

a) $R_1$ and $R_2$ together form

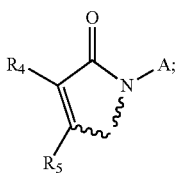

$R_3$ is absent;
Z is O; and
$R_4$ and $R_5$ may be the same or different and are each independently selected from H, a substituted or unsubstituted straight or branched $C_1$-$C_6$ alkyl group, a substituted or unsubstituted aliphatic cyclic group, a substituted or unsubstituted aromatic group and a substituted or unsubstituted heterocyclic group;

b) $R_1$ and $R_3$ together form

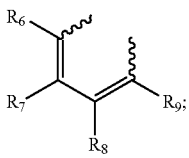

$R_2$ is

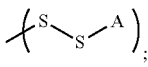

Z is N; and
each of $R_6$ to $R_9$ is independently selected from H a substituted or unsubstituted straight or branched $C_1$-$C_6$ alkyl group, a substituted or unsubstituted aliphatic cyclic group, a substituted or unsubstituted aromatic group and a substituted or unsubstituted heterocyclic group;

c) $R_1$ is

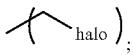

$R_2$ is A;
$R_3$ is absent;
Z is O; and
halo is a halogen;

d) $R_1$ is

$R_2$ is A;
$R_3$ is absent;

Z is O; and
B is —$NH_2$ or —$(CH_2)_n$—$ONH_2$, wherein n is from 1 to 6 and wherein in a), b) c) and d) A comprises the following structure:

X-L-M wherein X is a mass marker moiety, L is a cleavable linker and M is a mass normalization moiety.

The term mass label used in the present context is intended to refer to a moiety suitable to label an analyte for determination. The term label is synonymous with the term tag. Throughout the present application the term Tandem Mass Tag (TMT) is synonymous with the term mass label.

The term mass marker moiety used in the present context is intended to refer to a moiety that is to be detected by mass spectrometry.

The term mass normalisation moiety used in the present context is intended to refer to a moiety that is not necessarily to be detected by mass spectrometry, but is present to ensure that a mass label has a desired aggregate mass. The mass normalisation moiety is not particularly limited structurally, but merely serves to vary the overall mass of the mass label.

Preferably, the mass normalisation moiety M attaches group A to the remainder of the mass label. However, it is also possible that the mass marker moiety X attaches group A to the remainder of the mass label.

In the embodiments a) to c) above novel compounds have been prepared to specifically label the sulfhydryl group found on the amino acid cysteine. Labelling of cysteine residues is preferred when the sample to be analysed is highly complex. Using currently known isobaric mass tags labelling occurs on alpha and epsilon amine groups representing the N-terminus and side chain of lysine residues respectively. In commonly used proteomic workflows proteins are digested using the enzyme trypsin prior to analysis. In so doing free N-termini are created which are available for labelling and so the whole sample complexity is present in the labelled peptide mix. Cysteine is a relatively rare amino acid and is only found in a small proportion of tryptic digest peptides. By labelling cysteine residues and subsequent removal of unlabelled species it is possible to dramatically reduce the complexity of a tryptic digest sample. This complexity reduction allows faster and more sensitive analysis by mass spectrometry and is highly desirable. EP 1105517 discloses a set of isotopic mass tags with cysteine reactivity wherein two samples can be analysed per experiment. In the present invention the principles of isobaric mass tags and complexity reduction through cysteine labelling are combined in a manner that allows the same workflow and analytical methods to be adopted from use of the amine labelling reagent described in WO 2007/012849. This has substantial benefits in terms of manufacturing costs where a common precursor can be applied, and in the time and cost of method development.

Embodiment b) above comprises the 2-dithiopyridine group and has several advantages: it shows a high selectivity to label cysteine residues, even at increased pH as often used in buffer solutions useful in proteomic investigations (eg. Triethylammonium bicarbonate TEAB) and it is not labile to exposure to water. Furthermore, this group can be re-cleaved from peptides easily if desired by treatment with any disulfide-reducing reagents.

In a preferred embodiment, $R_1$ and $R_2$ together form

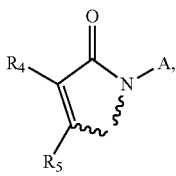

$R_3$ is absent, Z is O, and $R_4$ and $R_5$ are both H.

In another embodiment, $R_1$ and $R_3$ together form

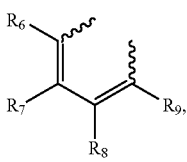

$R_2$ is

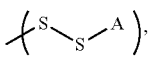

Z is N, and each of $R_6$ to $R_9$ is H.

In a further embodiment, $R_1$ is

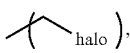

$R_2$ is A, $R_3$ is absent and Z is O.

In embodiment d) above a set of isobaric mass tags with selective reactivity for carbonyl groups such as aldehydes and ketones is disclosed. Aldehyde and ketone groups are found naturally on complex bioactive molecules such as steroids and may also be present in proteins and glycoproteins that have been subjected to oxidation. An isobaric mass tag with selective reactivity for carbonyl groups may therefore have a wide range of utilities. A number of chemical groups are able to react with ketones and in the present invention the hydrazide and aminoxy groups have been attached to the core molecule to produce sets of carbonyl-selective isobaric mass tags.

Preferably, $R_1$ is

$R_2$ is A, $R_3$ is absent, Z is O, and B is —$NH_2$.

In another embodiment, $R_1$ is

$R_2$ is A, $R_3$ is absent, Z is O, and B is —$(CH_2)_3$—$ONH_2$.

In a further aspect of the invention, provided is a reactive mass label for labelling a biological molecule for detection by mass spectrometry, wherein the mass label comprises the following structure:

X-L-M-Re wherein X is a mass marker moiety, L is a cleavable linker, M is a mass normalization moiety, and Re is a reactive functionality for attaching the mass label to a biological molecule comprising the following structure:

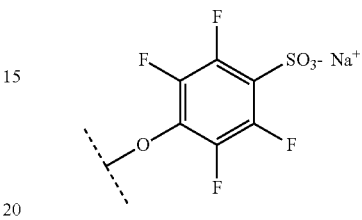

Such reactive mass labels have improved aqueous solubility and stability. The majority of mass tags carry a succinimide ester group to allow efficient labelling of amine functions on peptides and proteins. Whilst the succinimide labelling reaction is rapid and can be driven to completion with relatively low molar excess, it is highly sensitive to hydrolysis of the succinimide ester. In certain applications such as labelling of cell surfaces it is necessary to employ a predominantly aqueous environment and the use of a standard succinimide ester is not possible. Improvements to succinimide esters have been made with sulfo-N-hydroxysuccinimide ester (sulfo-NHS) showing a greater resistance to hydrolysis than the non-sulfonated parent. An additional benefit of the sulfo-NHS type of group is that it renders the tandem mass tag highly polar and prevents uptake of tags into the cell through the intact cell membrane. Consequently the sulfo-NHS derivatives of TMT are specifically able to label extracellular proteins. However, removal of free sulfo-NHS during mass tag manufacture can be problematic. To circumvent this, the present inventors discovered that a sulfo-tetrafluorophenyl moiety could be used.

In another aspect of the invention, provided is a reactive mass label for labelling a biological molecule for detection by mass spectrometry, wherein the mass label comprises the following structure:

X-L-M-S—Re wherein X is a mass marker moiety, L is a cleavable linker, M is a mass normalization moiety, S is a mass series modifying group comprising the following group:

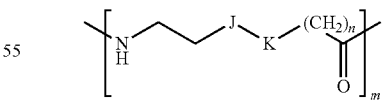

wherein J is C=O, K is NH, and n is 2 or J and K are both $CH_2$ and n is 1, and wherein m is at least 1; and Re is a reactive functionality for attaching the mass label to a biological molecule.

The limitation on the multiplexing rate for a single isobaric mass tag set can be overcome by providing multiple sets each carrying a unique additional mass. The additional mass is provided by the mass series modifying group. This concept is described in U.S. Pat. No. 7,294,456 which is incorporated herein. In the present invention the inventors found that it was possible to develop arrays of isobaric mass tag sets by adding additional beta-alanine moieties into the linker region of the DMPip-βALA core structure. Such a unitary approach provides a rapid and inexpensive means of increasing the multi- plexing rate from 6 to 12, 18, 24 or more samples. It is a major advantage of this invention that the behaviour of the mass reporters in each isobaric set within the array behaves in exactly the same way as the already established Tandem Mass Tag reporters disclosed in WO 2007/012849. Because incorporation of one or two beta-alanines introduces additional labile amide bonds an alternate approach using aminohexanoic acid. The skilled person will understand that the specific means of introducing add masses to the DMPip-βALA core structure is not particularly limiting and alternate means are considered to be within the scope of the present invention.

Preferably, the reactive functionality is as defined in any of a) to d) above or comprises the sulfo-tetrafluorophenyl moiety.

In another preferred embodiment the reactive functionality comprises the following group:

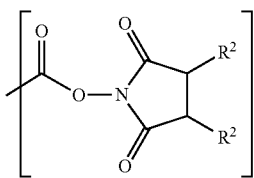

wherein each $R^2$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group.

In any of the above embodiments of the invention, preferably the cleavable linker L comprises an amide bond.

In a preferred embodiment of any of the aspects of the invention the mass marker moiety X comprises the following group:

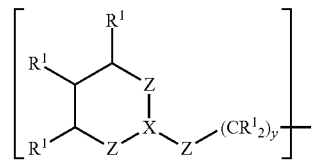

wherein the cyclic unit is aromatic or aliphatic and comprises from 0-3 double bonds independently between any two adjacent atoms; each Z is independently N, N($R^1$), C($R^1$), CO, CO($R^1$), C($R^1$)$_2$, O or S; X is N, C or C($R^1$); each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10.

The mass marker moiety may comprise a group selected from the following groups:

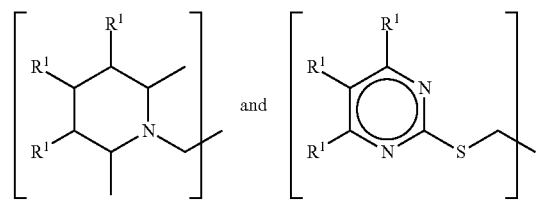

Preferably, the mass marker moiety comprises a group selected from the following groups:

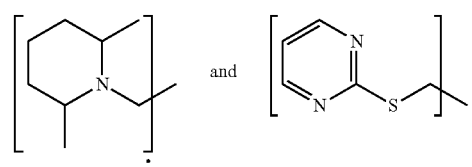

More preferably, the reactive mass label has one of the following structures:

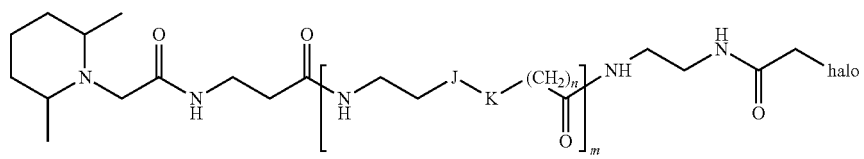

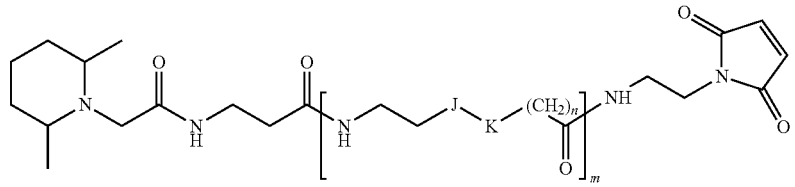

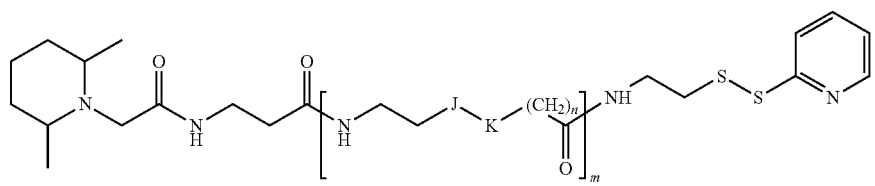

wherein J is C=O, K is NH, and n is 2;
or J and K are both CH$_2$ and n is 1; and
wherein m is any positive integer including 0.

In preferred embodiments, m=0 and the reactive mass label has one of the following structures:

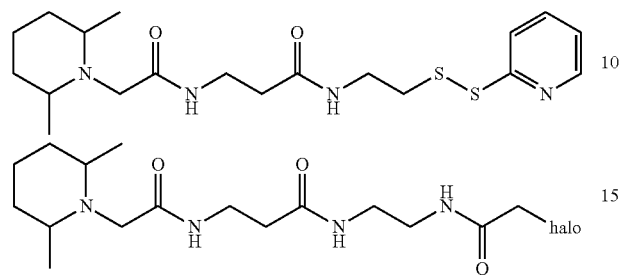

-continued

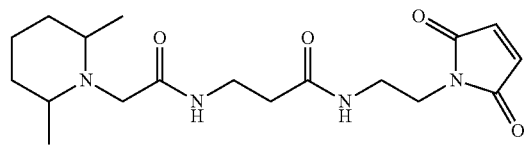

These labels react with the thiol groups of cysteine residues.

In another preferred embodiment, the reactive mass label has one of the following structures:

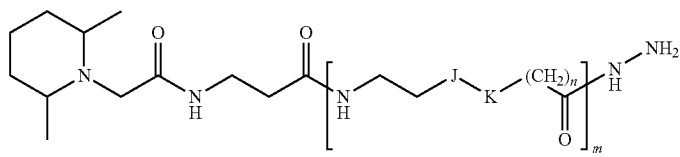

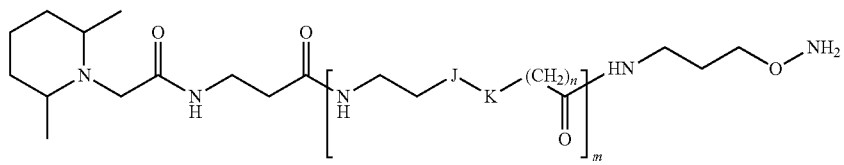

wherein J is C=O, K is NH, and n is 2;
or J and K are both CH$_2$ and n is 1; and
wherein m is any positive integer including 0.

In preferred embodiments, m=0 and the reactive mass label has one of the following structures:

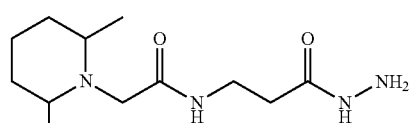

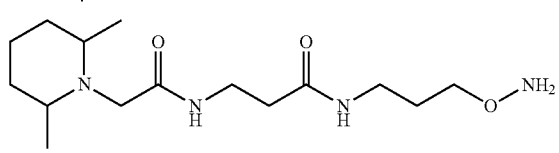

These labels react with carbonyl groups, such as those found in steroid hormones.

In a further preferred embodiment, the reactive mass label has the following structure:

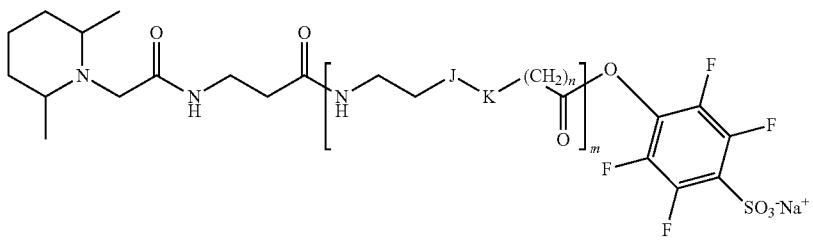

wherein J is C=O, K is NH, and n is 2;
or J and K are both CH$_2$ and n is 1; and
wherein m is any positive integer including 0.

Preferably, m is 0 and thus the label has the following structure:

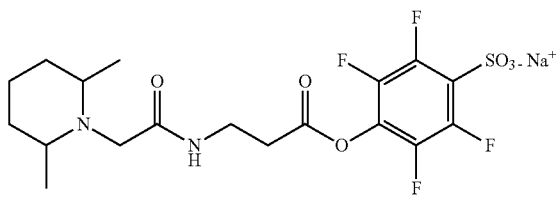

In a further preferred embodiment, the reactive mass label has one of the following structures:

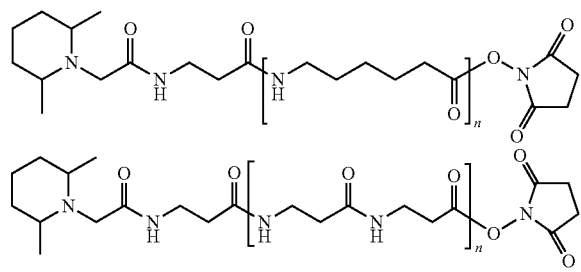

wherein n is at least 1.

Preferably, n is 1 and therefore the mass label has one of the following structures:

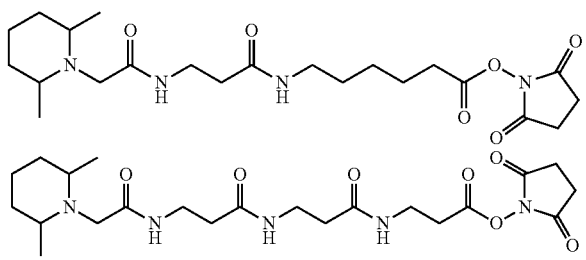

In another aspect the invention provides a set of two or more reactive mass labels, wherein each label in the set is as defined above and wherein each mass normalisation moiety ensures that a mass label has a desired aggregate mass, and wherein the set comprises:

a group of labels having a mass marker moiety of common mass, each label in the group having a unique aggregate mass; or a group of labels having a mass marker moiety, each mass marker moiety having a mass different from that of all other mass marker moieties in that group, and each label in the group having a common aggregate mass;

and wherein all the mass labels in the set are distinguishable from each other by mass spectroscopy.

In one embodiment, each label in the set comprises a mass marker moiety having a common mass and each label in the set has a unique aggregate mass. In another embodiment, each label in the set comprises a mass marker moiety having a unique mass and each label in the set has a common aggregate mass.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety and any other components of the mass label.

The mass normalisation moiety is only limited by its mass, which may vary between different mass labels in a set. For instance, where a set comprises a group of labels having mass marker moieties of different masses but a common aggregate mass, the mass of the mass normalisation moiety will be different in each mass label in the set. In this case, the mass of the mass normalisation moiety in each individual mass label will be equal to the common aggregate mass minus the mass of the particular mass marker moiety in that mass label and minus the mass of the cleavable linker. Where the set comprises a group of labels having a mass marker moiety of common mass but different aggregate masses, it is clear that the mass of the mass normalisation moiety will need to vary such that the aggregate mass of all labels in the group is different.

All mass labels in the set are distinguishable from each other by mass spectroscopy. Therefore, a mass spectrometer can discriminate between the mass labels, i.e. the peaks derived from individual mass labels can be clearly separated from one another. The difference in mass between the mass marker moieties or the mass labels means that a mass spectrometer can discriminate between ions derived from different mass labels or mass marker moieties.

Preferably, each mass label in the set comprises A which has the following structure:

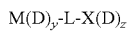

wherein M is a mass normalisation moiety, X is a mass marker moiety, D is a mass adjuster moiety, L is a cleavable linker, y and z are integers of 0 or greater, and y+z is an integer of 1 or greater.

The mass adjuster moiety is preferably selected from:
(a) an isotopic substituent situated within the mass marker moiety and/or within the mass normalisation moiety, and
(b) substituent atoms or groups attached to the mass marker moiety and/or attached to the mass normalisation moiety.

Typically the mass adjuster moiety is selected from a halogen atom substituent, a methyl group substituent, and $^2$H, $^{15}$N, $^{13}$C or $^{18}$O isotopic substituents.

In one preferred embodiment of the invention, each mass label in the set comprises A which has the following structure:

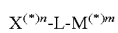

wherein X is the mass marker moiety, L is the cleavable linker and M is the mass normalisation moiety, and * is an isotopic mass adjuster moiety, and n and m are integers of 0 or greater such that either:

each label in the set comprises a mass marker moiety having a common mass and each label in the set has a unique aggregate mass; or each label in the set comprises a mass marker moiety having a unique mass and each label in the set has a common aggregate mass.

Preferably, the set of reactive mass labels comprises two or more mass labels of any of the following structures:

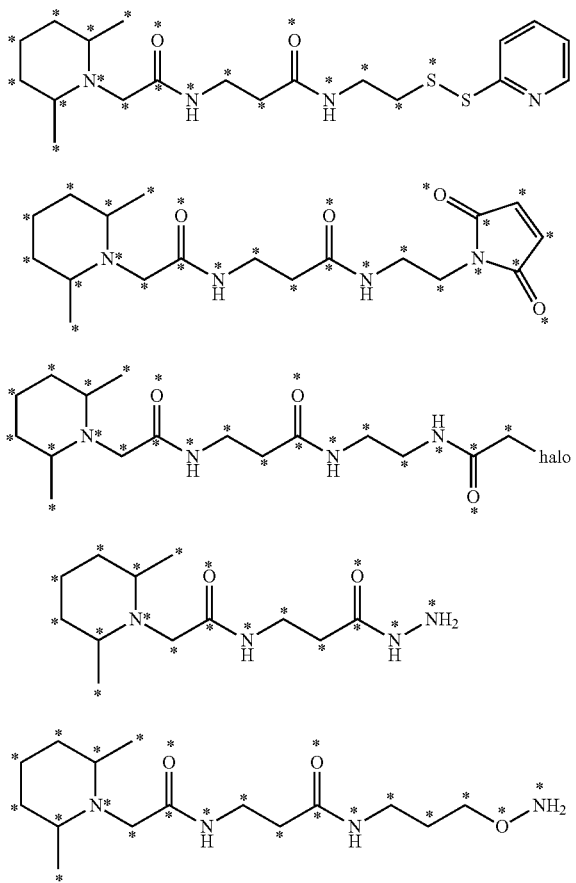

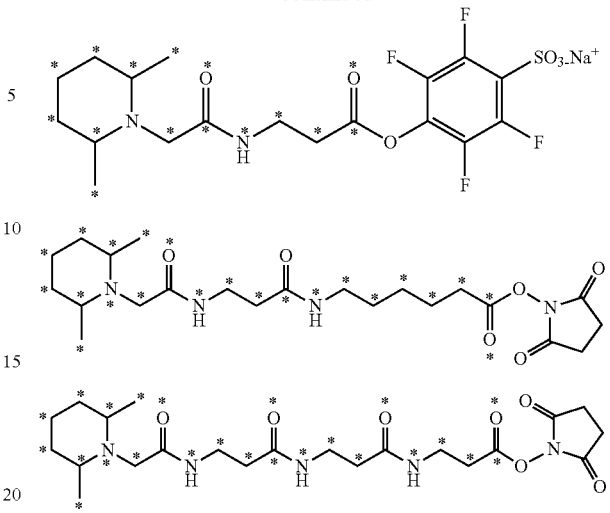

wherein * represents that the oxygen is $O^{18}$, carbon is $C^{13}$ or the nitrogen is $N^{15}$, and wherein the each label in the set comprises one or more * such that either:

each label in the set comprises a mass marker moiety having a common mass and each label in the set has a unique aggregate mass; or each label in the set comprises a mass marker moiety having a unique mass and each label in the set has a common aggregate mass.

It is preferred that in the leaving groups of label reagents (for example, thiopyridine, succinimide moieties), no heavy isotopes are present.

In a particularly preferred embodiment, the mass adjuster moiety * is $C^{13}$ or $N^{15}$ and the set comprises six reactive mass labels having the following structures:

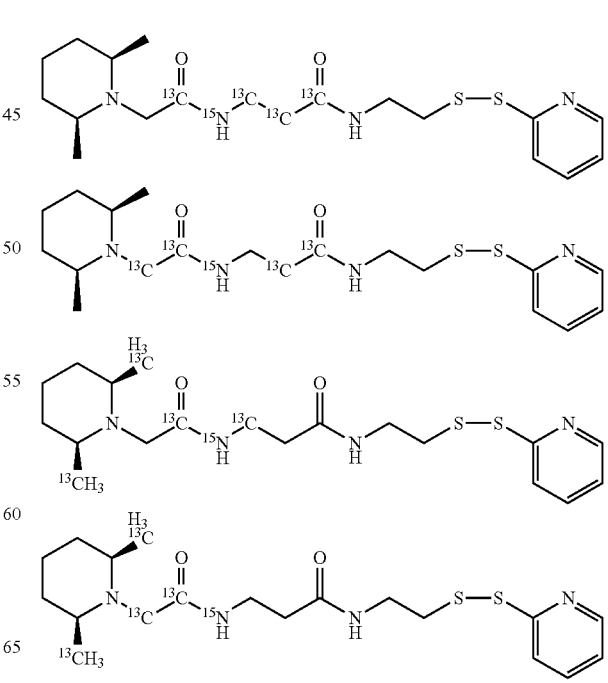

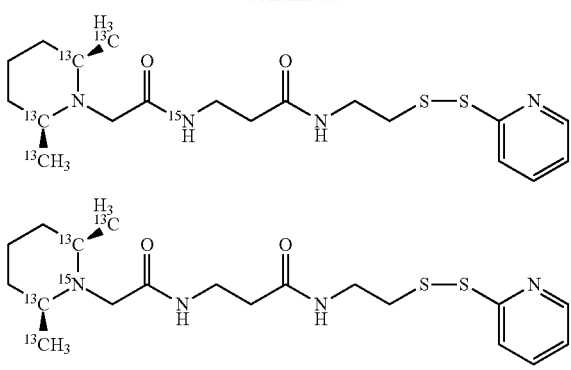

In another preferred embodiment the mass adjuster moiety * is $C^{13}$ or $N^{15}$ and the set comprises six reactive mass labels having the following structures:

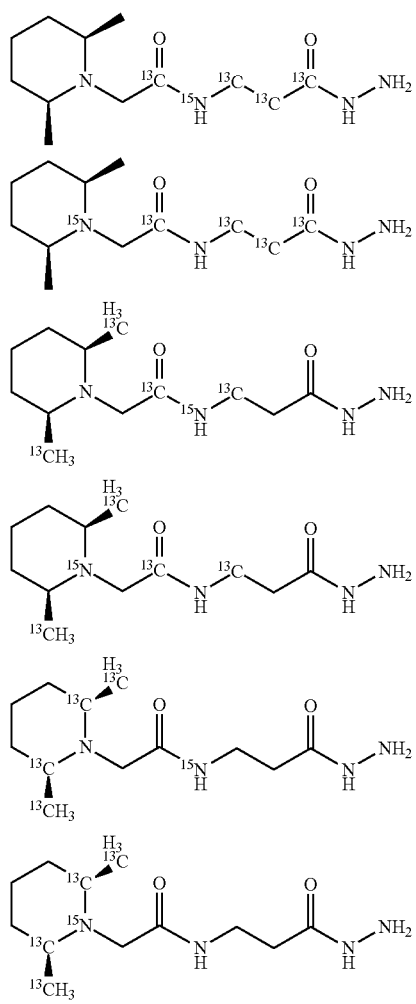

Alternatively, the mass adjuster moiety * is $C^{13}$ or $N^{15}$ and the set comprises six reactive mass labels having the following structures:

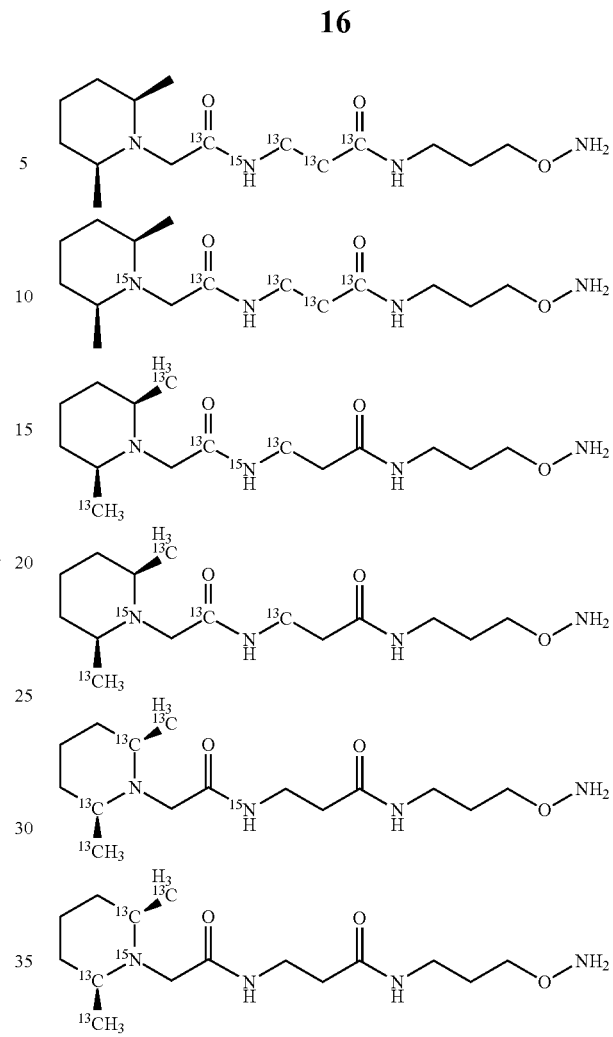

In a further aspect of the invention, provided is an array of mass labels, comprising two or more sets of mass labels as defined above, wherein the aggregate mass of each of the mass labels of any one set in the array is different from the aggregate mass of each of the mass labels of every other set in the array.

The aim of this aspect of the invention is to increase the number of samples (multiplexing rate) that can be analysed in a single experiment. When increasing the multiplexing rate it is necessary to consider the relationship between the number of samples and sensitivity in MS/MS analysis. It is understood by the skilled person that in the first stage of an MS/MS experiment ions of the desired mass to charge ratio are accumulated in a collision cell that has a finite capacity. The trapped ions are then fragmented and the fragments allowed to pass through to the detector where the mass-to-charge ratio and abundance are determined. If too many samples are included there is a risk that the number of fragments released into the detector will be below the limit of detection of the instrument. As a rule of thumb the greater the number of isobaric samples are present the lower the sensitivity becomes.

Preferably, each mass label in at least one set comprises a mass series modifying group of a common mass, the mass series modifying group in each of the mass labels of any one set having a different mass from the mass series modifying groups in each of the mass labels of every other set in the array. The mass series modifying group separates the masses of the sets from each other.

In a preferred array, each mass label in at least one set comprises a mass series modifying group comprising the following group:

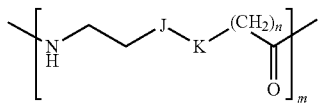

wherein J is C=O, K is NH, and n is 2 or J and K are both $CH_2$ and n is 1, and wherein m is at least 1; and the mass series modifying group of each of the mass labels of any one set has a different mass from the mass series modifying groups in each of the mass labels of every other set in the array due to the presence of a different number of isotopic mass adjuster moieties *.

In a particularly preferred embodiment the array of mass labels comprises:

a) a first set of mass labels, wherein each mass label in the set comprises a mass modifying group having the following structure:

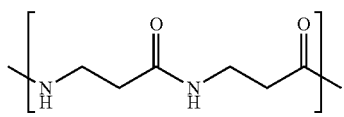

b) a second set of mass labels, wherein each mass label in the set comprises a mass modifying group having the following structure:

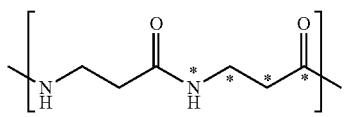

and;

c) a third set of mass labels, wherein each mass label in the set comprises a mass modifying group having the following structure:

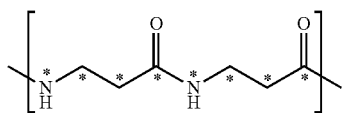

A further aspect of the invention is provided by use of a reactive mass label as defined above in a method of analysis by mass spectrometry.

Also provided is a method of analysis, which method comprises detecting a biological molecule by identifying by mass spectrometry a mass label relatable to the biological molecule, wherein the mass label is a mass label as defined above.

Preferably, the method comprises the following steps:
1. reacting the biological molecule with a reactive mass label as defined above;
2. separating the labelled biological molecule;
3. identifying by mass spectrometry the mass label relatable to the biological molecule.

The invention will now be described in further detail by way of example only, with reference to the accompanying drawings, in which.

Figure 3:
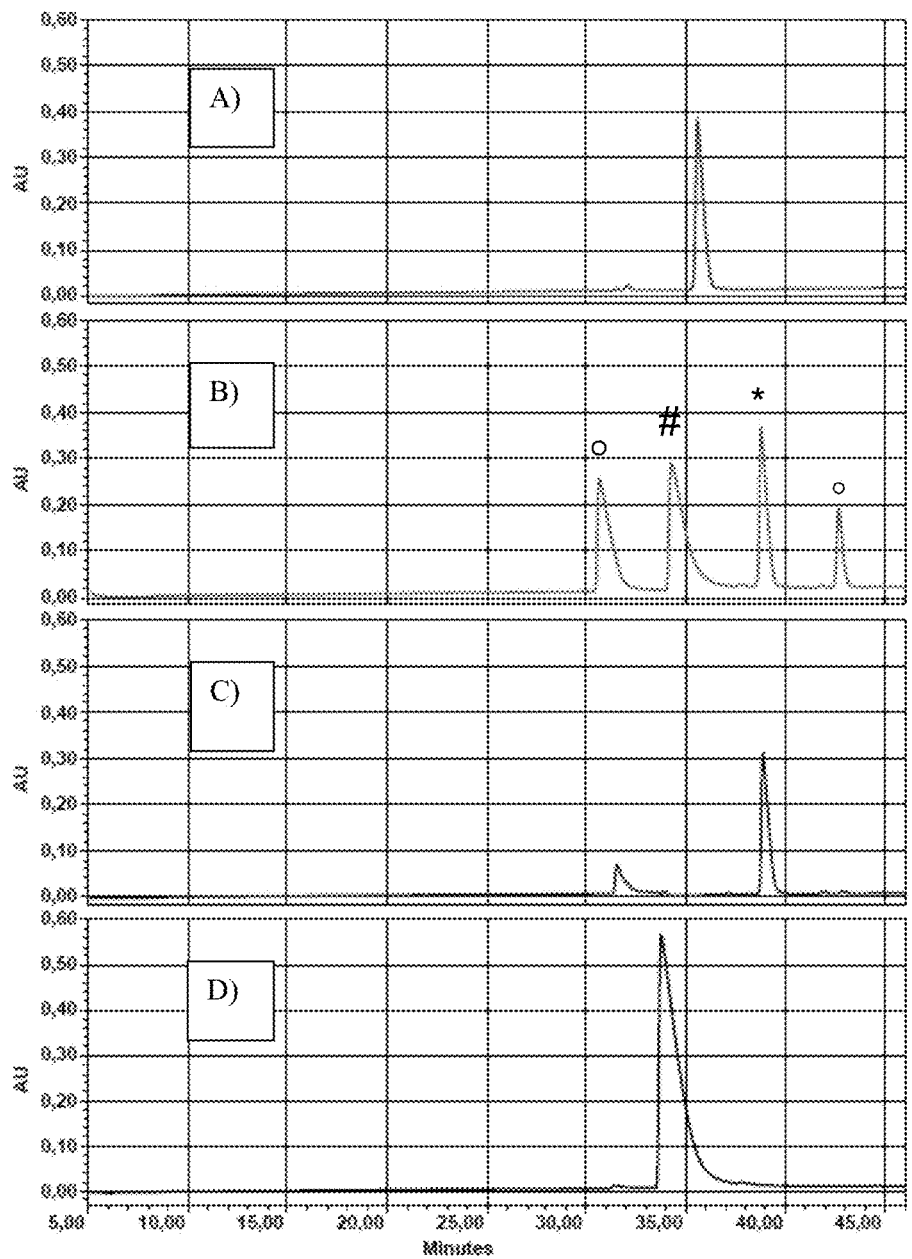

FIG. 3 shows monitoring of the labelling reaction of a Cys-containing peptide (VATVCLPR) with DMPip-bALA-DTP. A) shows the native peptide, B) shows the crude reaction mixture after reduction and labelling wherein * is the labelled peptide, # is the mass label and ° are reagent-specific side products, C) shows the purity of the labelled peptide after purification, no unlabelled native peptide is observed. D) shows the DMPip-bALA-DTP reagent.

Figure 4:
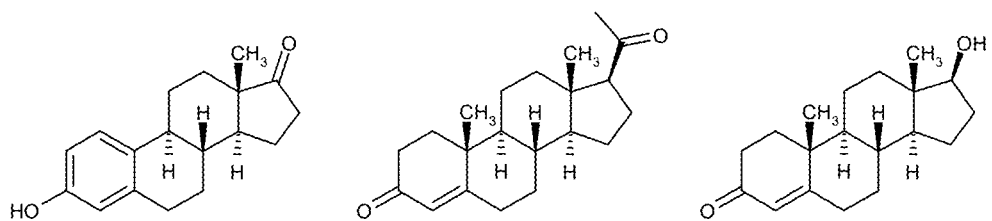

FIG. 4 shows selected steroid structures: estrone (left), progesterone (middle), testosterone (right).

Figure 5:
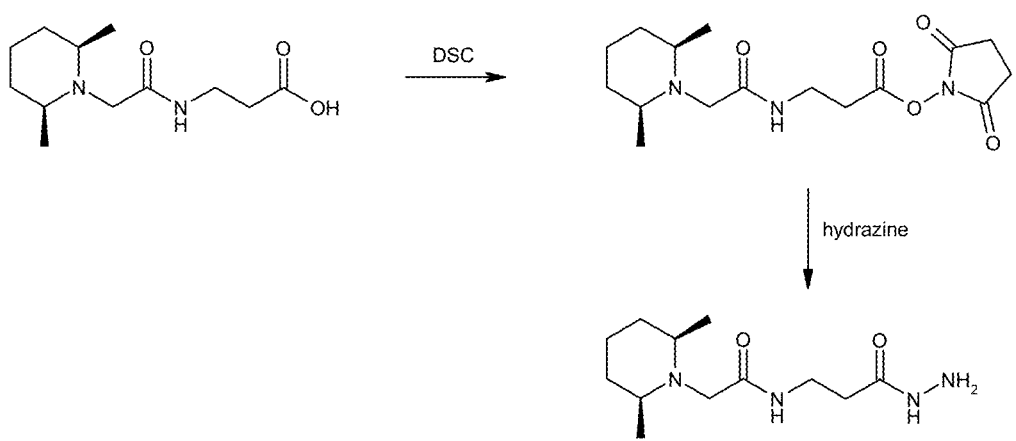

FIG. 5 shows a reaction scheme for the synthesis of a hydrazide mass label which is capable of reacting with carbonyl groups.

Figure 6:
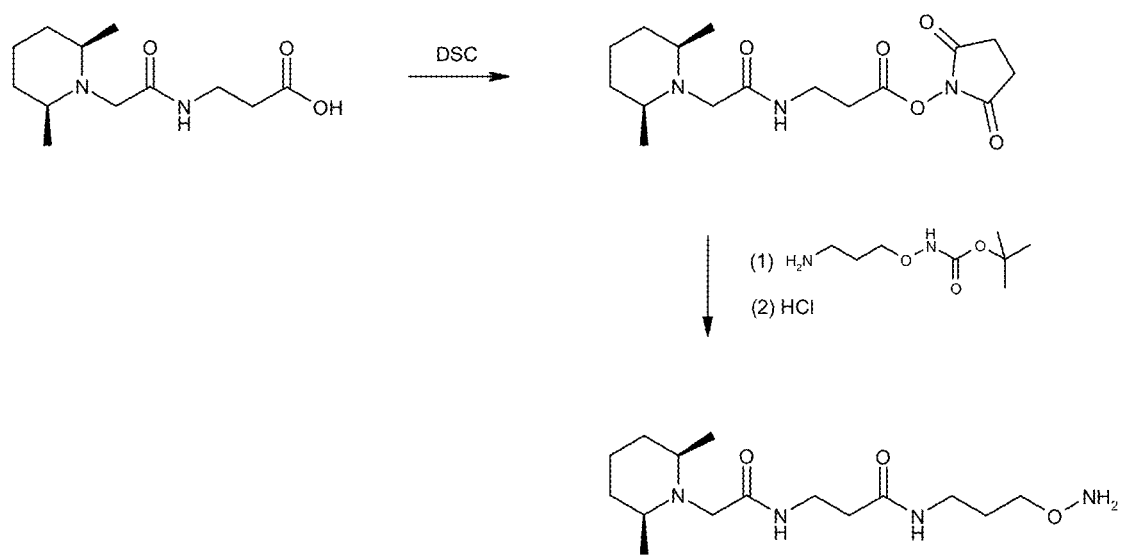

FIG. 6 shows a reaction scheme for the synthesis of an aminoxypropyl mass label which is capable of reacting with carbonyl groups.

Figure 7:
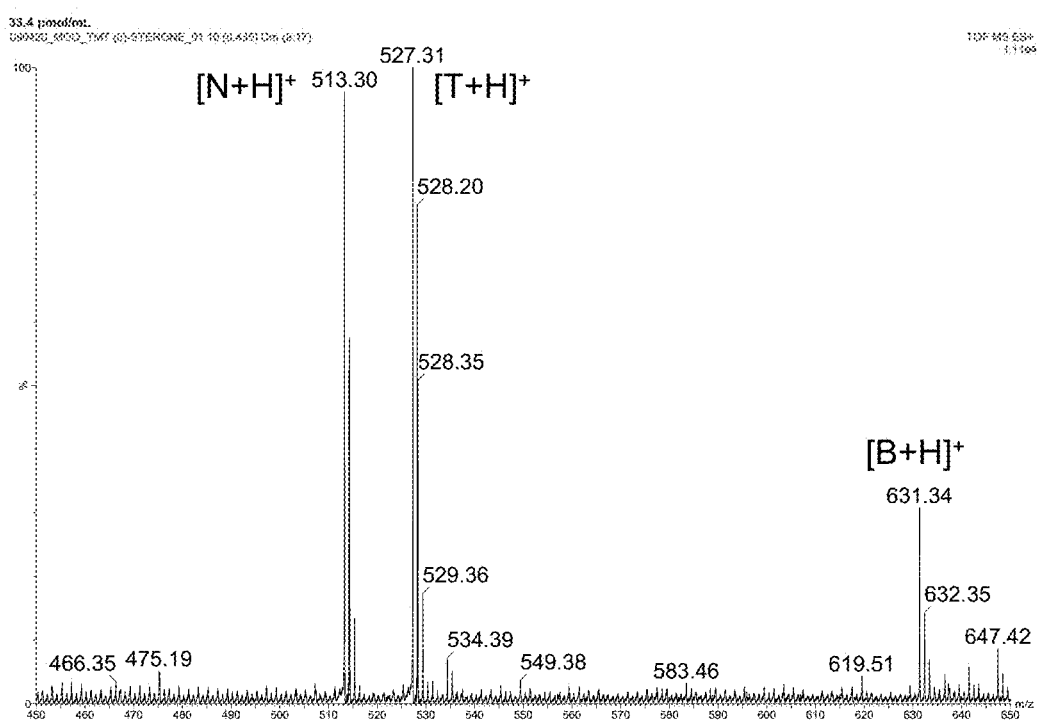

FIG. 7 shows a mass spectrum of testosterone (T), nandrolone (N) and betamethasone (B) derivatized with mass labels.

Figure 8:
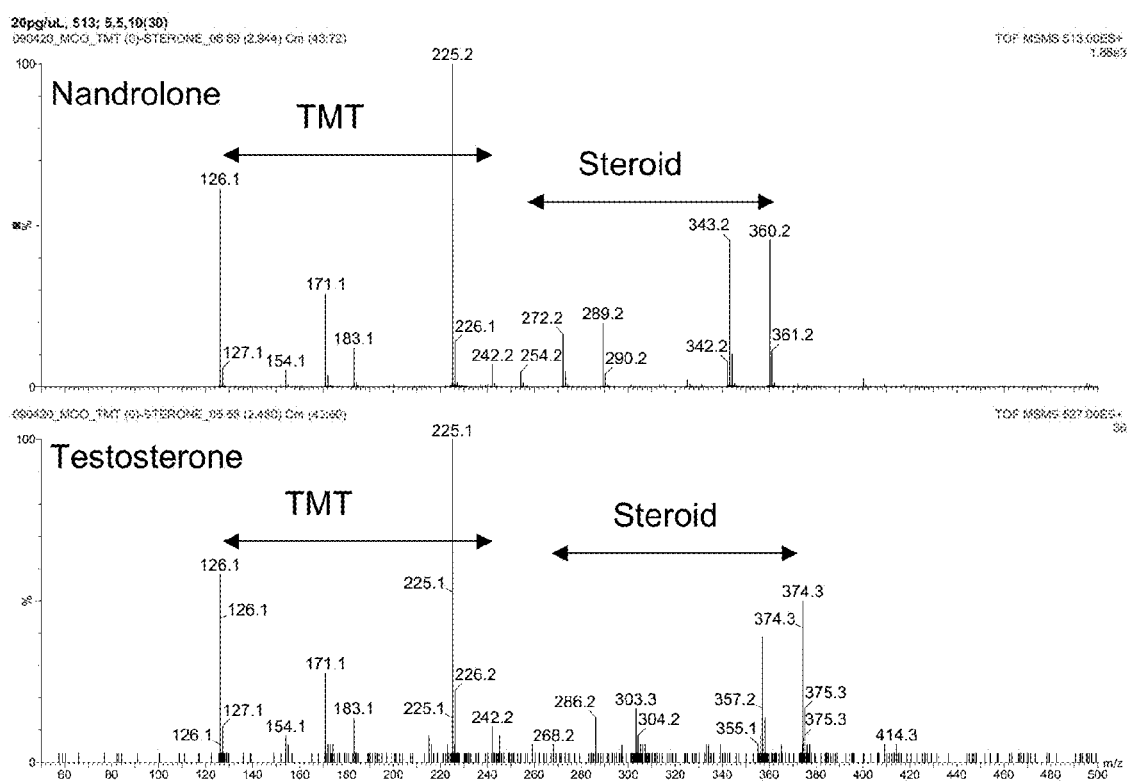

FIG. 8 shows an MS/MS spectrum of mass-labelled nandrolone and testosterone.

FIG. 9 shows structures of TMT mass labels in hydrazide form: FIG. 9(A) shows TMTzero hydrazide, FIG. 9(B) shows TMTduplex hydrazide ($TMT^2$-126 hydrazide (left), $TMT^2$-127-hydrazide (right)), FIG. 9(C) shows TMTsixplex-hydrazide ($TMT^6$-126 hydrazide (upper left) to $TMT^6$-131 hydrazide (lower right)).

FIG. 10 shows structures of TMT mass labels in aminoxypropyl amide form: FIG. 10(a) shows TMTzero aminoxy, FIG. 10(B) shows TMTduplex aminoxy ($TMT^2$-126 aminoxy (left), $TMT^2$-127 aminoxy (right)), FIG. 10(C) shows TMTsixplex aminoxy ($TMT^6$-126 aminoxy (upper left) to $TMT^6$-131 aminoxy (lower right)).

Figure 11:
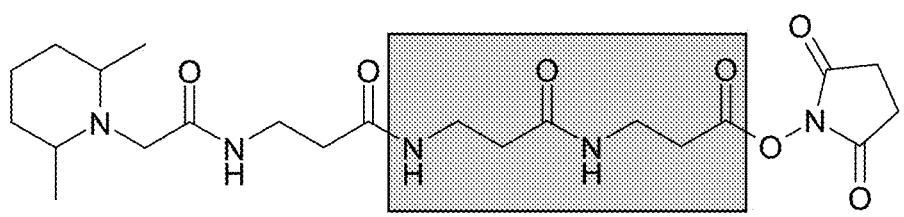
Figure 11:
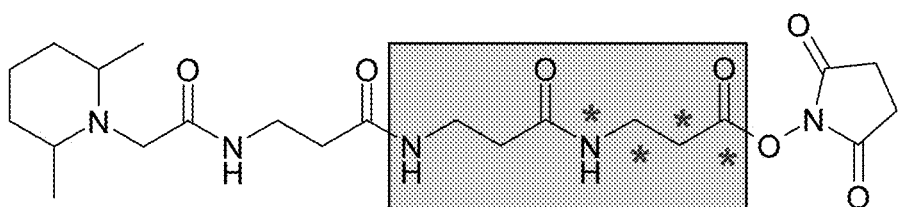
Figure 11:
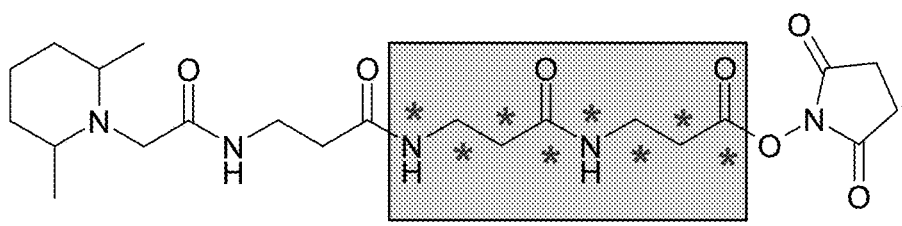

FIG. 11 shows a known mass label structure extended by two β-alanine building blocks in different combinations to achieve a multiplex rate of 18.

Figure 12:
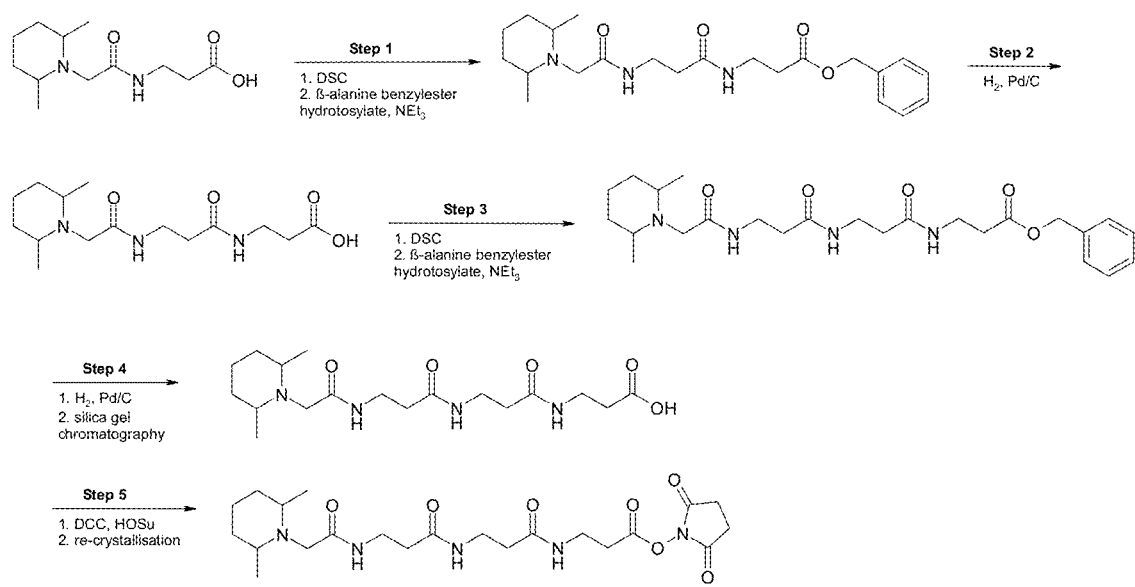
Figure 13:
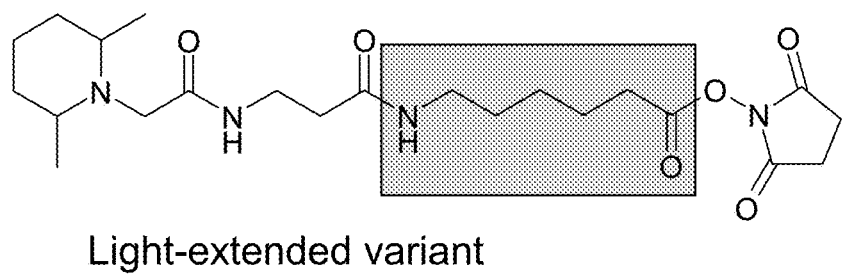
Figure 13:
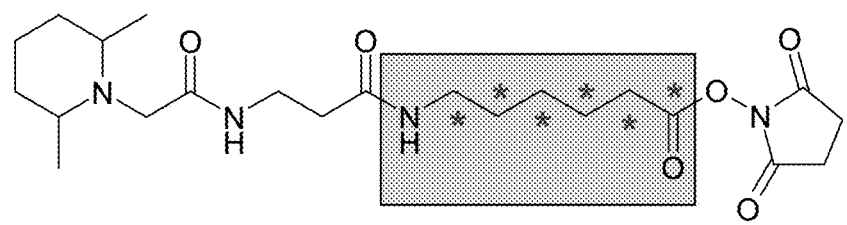

FIG. 12 shows a synthetic pathway for mass label arrays using DMP-(bAla)$_3$-OSu FIG. 13 shows a known mass label structure extended by one aminohexanoic acid building block to achieve a multiplex rate of 12 with a mass difference of 6.

Figure 14:
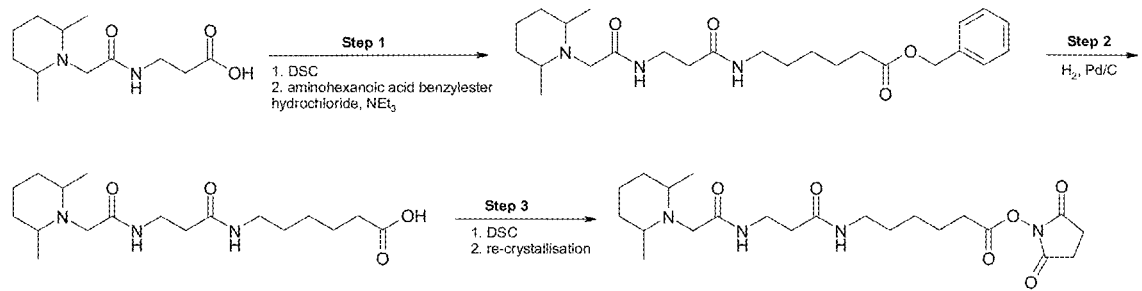

FIG. 14 shows a synthetic route for the generation of mass labels extended by an aminohexanoic acid moiety.

Figure 15:
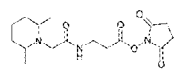
Figure 15:
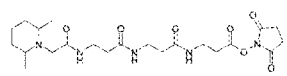
Figure 15:
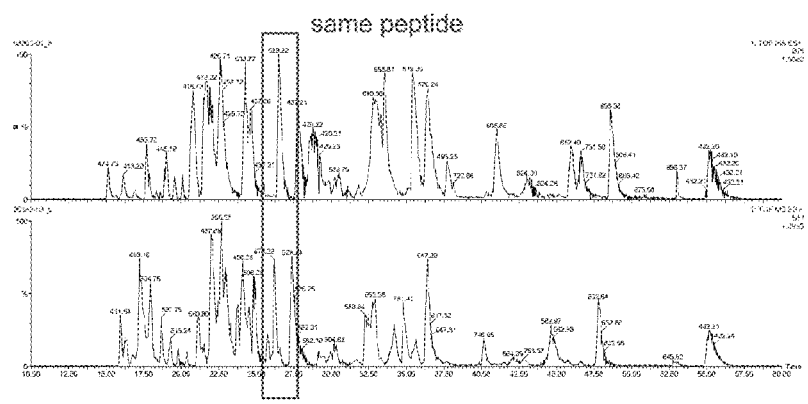
Figure 15:
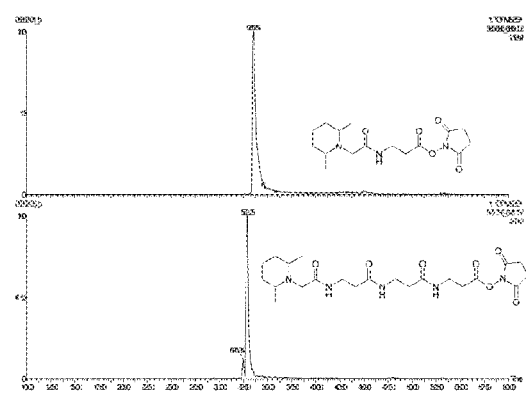
Figure 15:
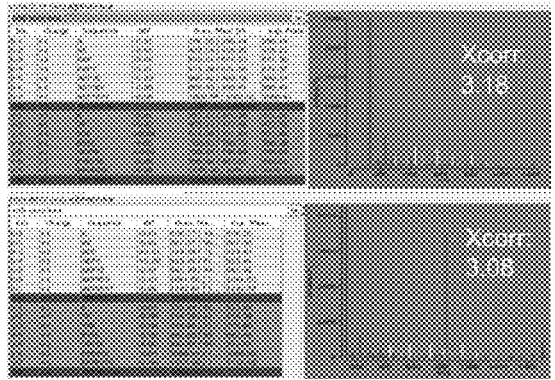

FIG. 15 shows data obtained from LC-MS/MS investigations of a tryptic digest of BSA labelled with either the standard TMT mass label (upper plots) or the mass labels extended by two beta-alanine moieties (lower plots). A) Base peak chromatograms are shown for both reagents with a peptide highlighted to indicate small shifts in retention time only. B) Left side shows mass traces for a given peptide to indicate once more a small retention time shift only. Right side shows MS/MS spectra of a peptide with assignment of b and y ions obtained after collision-induced dissociation. Data base searches succeeded similarly for both label reagents as shown by similar Xcorr factors from a Sequest search.

Figure 16:
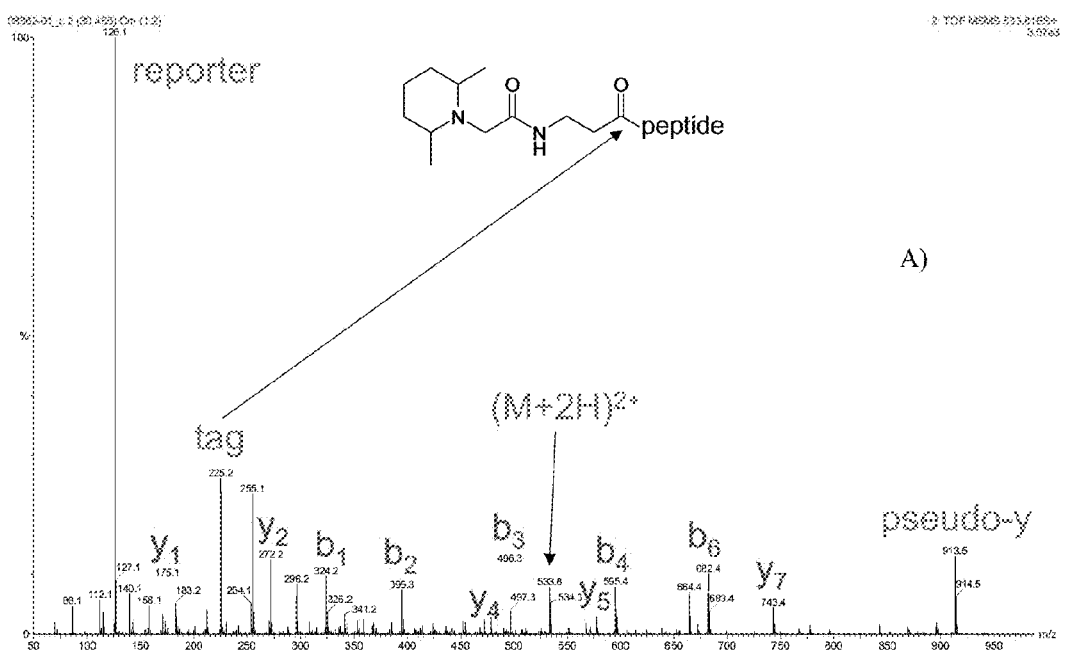
Figure 16:
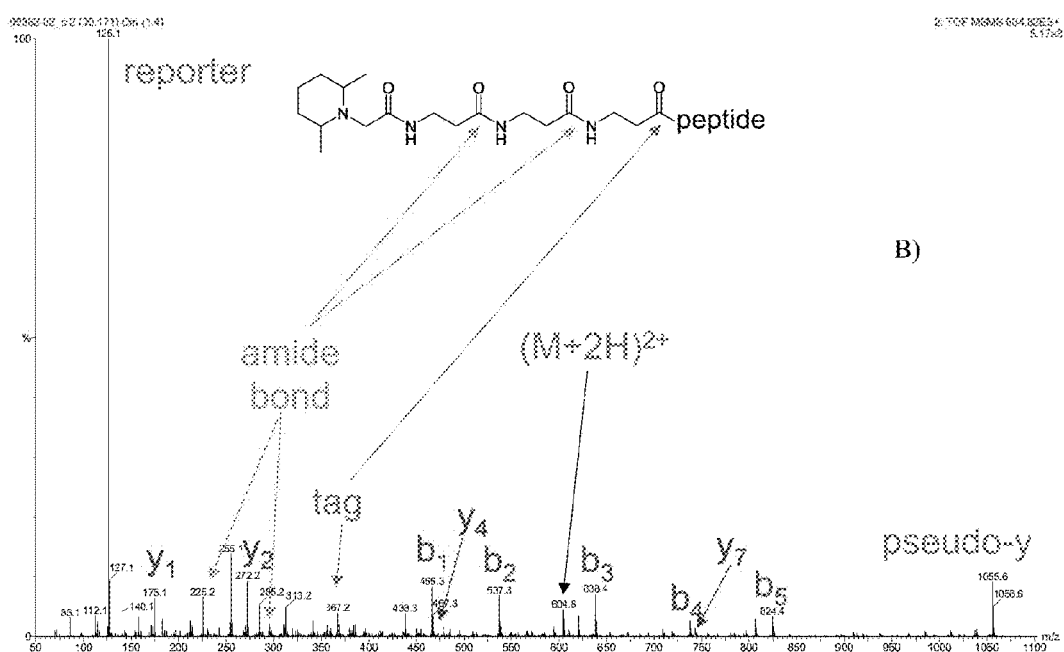

FIG. 16 shows data obtained from detailed investigations of additional fragments of both the known TMT reagent and the 2× beta-alanine extended one of the invention. A) A typical fragment pattern obtained from a standard TMT-labelled peptide. Beside the b and y ions and residual precursor, three TMT-related fragments are observed, the reporter ion (having the highest intensity), and both the tag ion (release of the entire label moiety) and the so-called pseudo-y ion, both of low intensity. B) The fragment pattern of the same peptide but labelled with the extended reagent is shown. Additionally to the fragments shown in A), two further tag-related fragments are observed. These can refer to fragmentation at the additionally introduced amide bonds as expected but are of low intensity only. Both the intensity of the reporter ion and the structural b and y ions are not reduced, thus relative quantitation and identification are not compromised.

Figure 17:
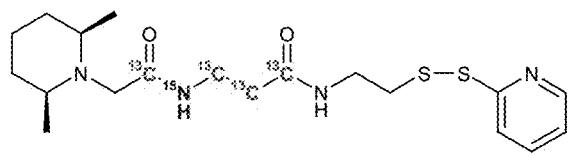
Figure 17:
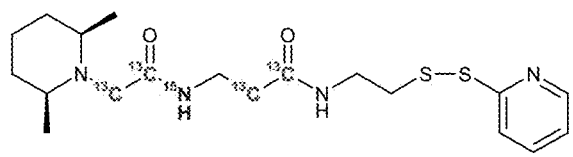
Figure 17:
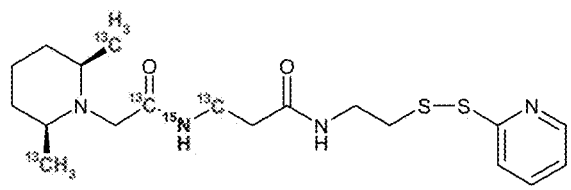
Figure 17:
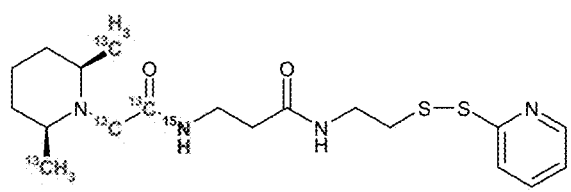
Figure 17:
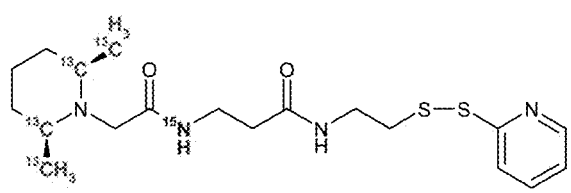
Figure 17:
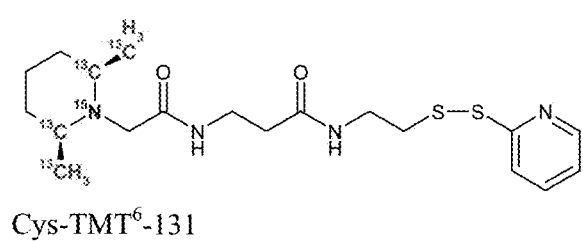
Figure 19C:
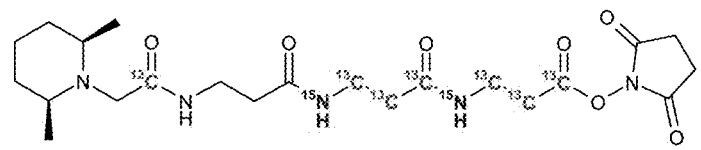
Figure 19C:
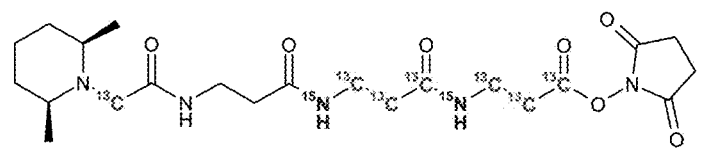
Figure 19D:
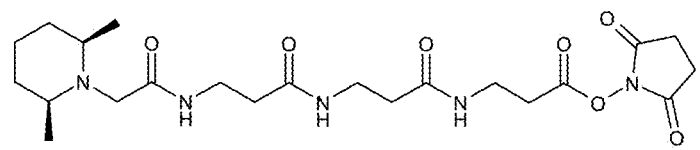
Figure 19D:
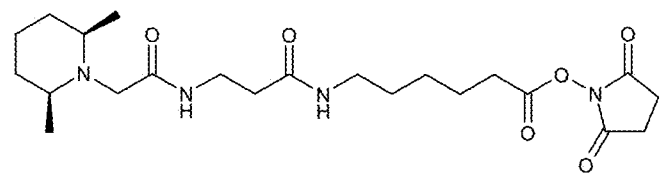

FIG. 17 shows a set of six thiol reactive mass labels, each having a molecular weight of 415.55 Da and a molecular formula $^{13}C4^{12}C15H30^{15}N^{14}N3O2S2$ FIG. 18(A) shows a set of two thiol reactive mass labels. FIG. 18 (B) shows a thiol reactive mass label without isotopic labelling.

FIG. 19 shows the structures of an array of mass labels comprising 4 sets of 2 mass labels. The standard labels have been extended using the β alanine dipeptide mass series modifying group.

The present invention will now be described in more detail.

Reactive Mass Label

The reactive mass label of the present invention for labelling a biological molecule for detection by mass spectroscopy comprises a reactive functionality for facilitating attachment of or for attaching the mass label to a biological molecule and a mass label A as defined below. In preferred embodiments of the present invention, the reactive functionality allows the mass label to be reacted covalently to an appropriate functional group in the biological molecule, such as, but not limited to, a nucleotide oligonucleotide, polynucleotide, amino acid, peptide, polypeptide or steroid hormone. The reactive functionality may be attached to the mass labels via a linker which may or may not be cleavable. The reactive functionality may be attached to the mass marker moiety of the mass label or the mass normalization moiety of the mass label.

A variety of reactive functionalities may be provided.

The reactive functionality may react with an amino group on the biological molecule, for example the ε-amino group of a lysine residue. In the simplest embodiments this may be an N-hydroxysuccinimide ester. However, the present inventors realised that there was a need to provide a range of mass labels which can react with functional groups other than amino groups.

Figure 1:
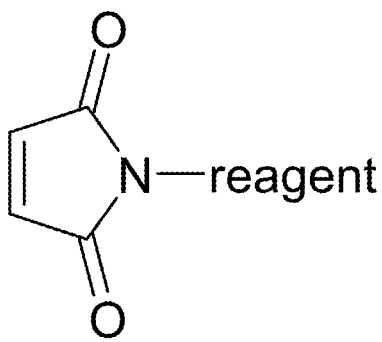
FIG. 1 shows different reactive groups able to react with cysteine residues. A) maleimido group, B) haloacetyl group (iodoacetyl, bromoacetyl), C) 2-dithiopyridine group.
Figure 1:
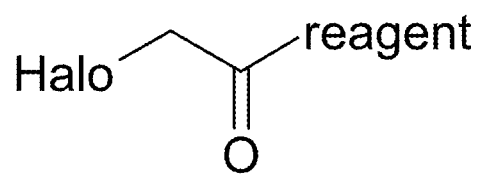
Figure 1:
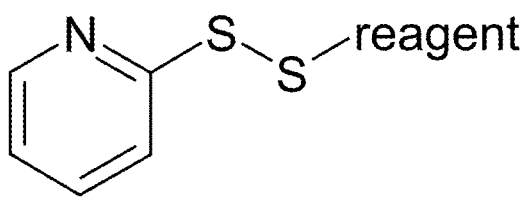

Therefore, the present inventors identified reactive functionalities which react with thiol groups in biological molecules. In particular these reactive functionalities are designed to react with the thiol group of a cysteine residue. Examples of reactive groups of the present invention which are able to react with cysteine residues are the maleimido, haloacetyl and 2-dithiopyridine groups as shown in FIG. 1. The thiol group of cysteine undergoes nucleophilic addition across the double bond of the maleimido group and undergoes nucleophilic substitution with the haloacetyl or 2-dithiopyridine group.

The present inventors have also designed mass labels with reactive functionalities which are capable of reacting with carbonyl or hydroxyl groups in biological molecules. In particular, these reactive functionalities are designed to react with the carbonyl or hydroxyl groups of steroid hormones. Reactive groups of the present invention which are able to react with carbonyl or hydroxyl groups in a biological molecule are hydrazide or —CONH—(CH$_2$)$_n$—ONH$_2$, wherein n is from 1 to 6, and preferably n is 3 i.e. aminoxypropyl amide (see FIGS. 5, 6, 9 and 10). These groups react with carbonyl groups to form hydrazones or O-alkyloximes respectively.

The present invention provides a reactive mass label for labelling a biological molecule for detection by mass spectrometry, which label comprises the following structure:

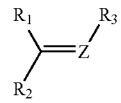

wherein $R_1$, $R_2$, $R_3$ and Z are selected from one of the following definitions a) to d):

a) $R_1$ and $R_2$ together form

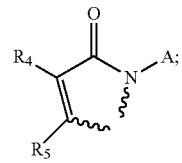

$R_3$ is absent;
Z is O; and
$R_4$ and $R_5$ may be the same or different and are each independently selected from H, a substituted or unsubstituted straight or branched $C_1$-$C_6$ alkyl group, a substituted or unsubstituted aliphatic cyclic group, a substituted or unsubstituted aromatic group and a substituted or unsubstituted heterocyclic group;

b) $R_1$ and $R_3$ together form

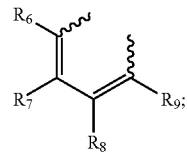

$R_2$ is

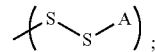

Z is N; and
each of $R_6$ to $R_9$ is independently selected from H a substituted or unsubstituted straight or branched $C_1$-$C_6$ alkyl group, a substituted or unsubstituted aliphatic cyclic group, a substituted or unsubstituted aromatic group and a substituted or unsubstituted heterocyclic group;

c) $R_1$ is

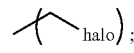

$R_2$ is A;
$R_3$ is absent;
Z is O; and
halo is a halogen;

d) $R_1$ is

$R_2$ is A;
$R_3$ is absent;
Z is O; and
B is —$NH_2$ or —$(CH_2)_n$—$ONH_2$, wherein n is from 1 to 6 and wherein in a), b) c) and d) A comprises the following structure:

X-L-M wherein X is a mass marker moiety, L is a cleavable linker and M is a mass normalization moiety.

The substituents $R_4$, $R_5$, $R_6$, $R_7$, $R_5$, $R_9$ are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

In a preferred embodiment, $R_1$ and $R_2$ together form

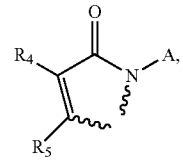

$R_3$ is absent, Z is O, and $R_4$ and $R_5$ are both H, i.e. the label comprises a maleimido group.

In another embodiment, $R_1$ and $R_3$ together form

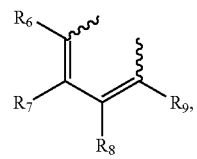

$R_2$ is

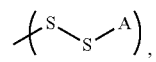

Z is N, and each of $R_6$ to $R_9$ is H, i.e. the label comprises a 2-dithiopyridine group.

In a further embodiment, $R_1$ is

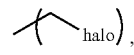

$R_2$ is A, $R_3$ is absent and Z is O, i.e. the label comprises a haloacetyl group. Preferably the halo group is iodo or bromo.

These 3 preferred embodiments all react with the thiol groups of cysteine residues.

Alternatively, $R_1$ is

$R_2$ is A, $R_3$ is absent, Z is O, and B is —$NH_2$.

In another embodiment, $R_1$ is

$R_2$ is A, $R_3$ is absent, Z is O, and B is —$(CH_2)_3$—$ONH_2$.

These 2 preferred embodiments react with the carbonyl groups of biomolecules.

Preferably, the mass normalisation moiety M attaches group A to the remainder of the mass label. However, it is also possible that the mass marker moiety X attaches group A to the remainder of the mass label.

The term mass label used in the present context is intended to refer to a moiety suitable to label an analyte for determination. The term label is synonymous with the term tag. Throughout the present application the term Tandem Mass Tag (TMT) is synonymous with the term mass label.

Mass Marker Moiety

The term mass marker moiety used in the present context is intended to refer to a moiety that is to be detected by mass spectrometry.

The components of the mass marker moiety of this invention are preferably fragmentation resistant so that the site of fragmentation of the markers can be controlled by the introduction of a linkage that is easily broken by Collision Induced Dissociation (CID).

The mass marker moiety of the present invention comprises the following group:

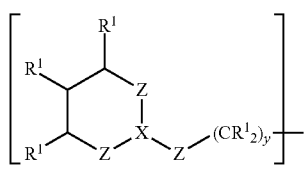

wherein the cyclic unit is aromatic or aliphatic and comprises from 0-3 double bonds independently between any two adjacent atoms; each Z is independently N, N($R^1$), C($R^1$), CO, CO($R^1$) (i.e. —O—C($R^1$)— or —C($R^1$)—O—), C($R^1$)$_2$, O or S; X is N, C or C($R^1$); each $R^I$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10, L is a cleavable linker comprising an amide bond and M is a mass normalization moiety.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In the present invention reference to the mass marker moiety comprising the group as defined above, means that the mass marker moiety may also comprise other groups depending upon where cleavage of the mass label occurs. In one embodiment where cleavage of the linker occurs at the amide bond between the CO and NH of the amide bond, the mass marker moiety may further comprise the CO group as shown below:

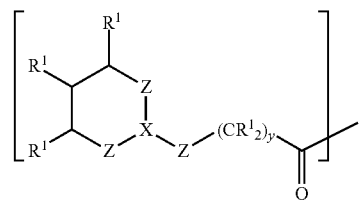

In an alternative embodiment, where the cleavage of the linker occurs at the bond after the NH group, the mass marker moiety may further comprise the CO and NH groups as shown below:

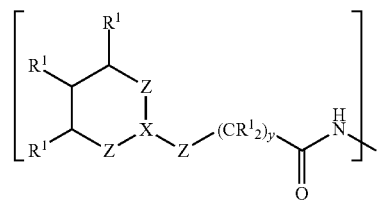

In a further alternative embodiment, where the linker cleaves before the CO group, the mass marker moiety only comprises the following group:

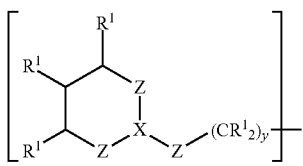

In a preferred embodiment, y is 0, 1 or 2, more preferably y is 0 or 1.

In one preferred embodiment the cyclic unit is aromatic and each Z in the cyclic unit is N. It is also preferred that X is C. It is also preferred that the Z not in the cyclic unit is S.

In an alternative preferred embodiment the cyclic unit is aliphatic and each Z in the cyclic unit is $C(R^1)_2$. It is also preferred that X is N. It is also preferred that the Z not in the cyclic unit is $C(R^1)_2$.

In a preferred embodiment the mass marker moiety comprises a group selected from the following groups:

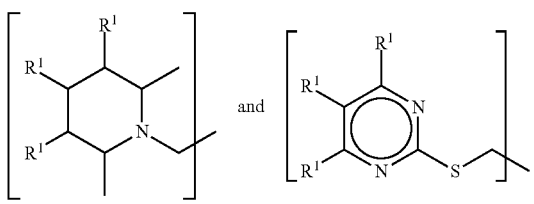

The above groups may also comprise other groups depending upon where cleavage of the mass label occurs. In one embodiment where cleavage of the linker occurs at the amide bond between the CO and NH of the amide bond, the above mass marker moiety groups may further comprise the CO group as shown below:

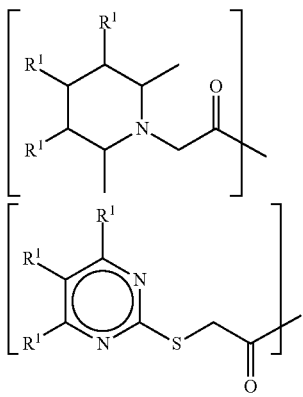

In an alternative embodiment, where the cleavage of the linker occurs at the bond after the NH group, the above mass marker moiety groups may further comprise the CO and NH groups as shown below:

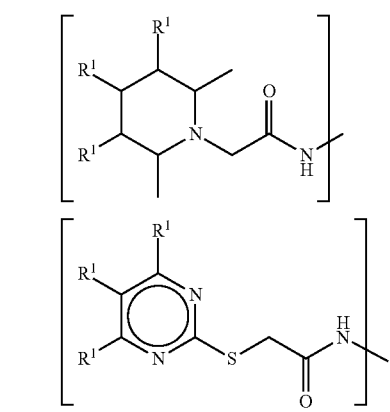

In a further alternative embodiment, where the linker cleaves before the CO group, the mass marker moiety only comprises the following group:

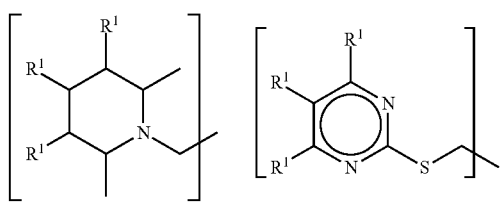

In a more preferred embodiment the mass marker moiety comprises a group selected from the following groups:

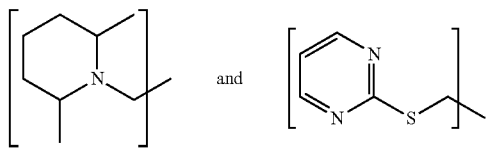

The above groups may also comprise other groups depending upon where cleavage of the mass label occurs. In one embodiment where cleavage of the linker occurs at the amide bond between the CO and NH of the amide bond, the above mass marker moiety groups may further comprise the CO group as shown below:

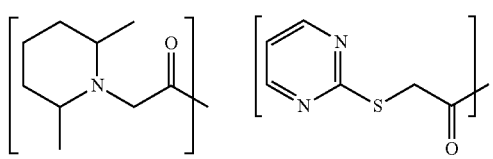

In an alternative embodiment, where the cleavage of the linker occurs at the bond after the NH group, the above mass marker moiety groups may further comprise the CO and NH groups as shown below:

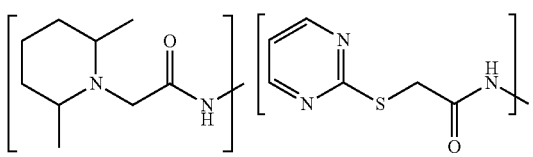

In a further alternative embodiment, where the linker cleaves before the CO group, the mass marker moiety only comprises the following group:

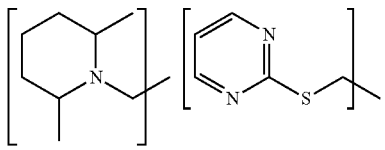

Linker

The structure of the linker is not particularly limited provided that it is cleavable. Preferably the linker comprises an amide bond. Preferably, the cleavable linker is a linker cleavable by collision. More preferably the linker consists of an amide bond.

In the discussion above and below reference is made to linker groups which may be used to connect molecules of interest to the mass label compounds of this invention. A variety of linkers is known in the art which may be introduced between the mass labels of this invention and their covalently attached biological molecule. Some of these linkers may be cleavable. Oligo- or poly-ethylene glycols or their derivatives may be used as linkers, such as those disclosed in Maskos, U. & Southern, E. M. Nucleic Acids Research 20: 1679-1684, 1992. Succinic acid based linkers are also widely used, although these are less preferred for applications involving the labelling of oligonucleotides as they are generally base labile and are thus incompatible with the base mediated de-protection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds of this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

Mass Normalisation Moiety

The structure of the mass normalization moiety of the mass label of the present invention is not particularly limited provided that it is suitable for ensuring that the mass label has a desired aggregate mass. However, the mass normalization moiety preferably comprises a straight or branched $C_1$-$C_{20}$ substituted or unsubstituted aliphatic group and/or one or more substituted or unsubstituted amino acids.

Preferably, the mass normalization moiety comprises a $C_1$-$C_6$ substituted or unsubstituted aliphatic group, more preferably a $C_1$, $C_2$, $C_3$, $C_4$, $C_5$ substituted or unsubstituted aliphatic group, still more preferably a $C_1$, $C_2$, or $C_5$ substituted or unsubstituted aliphatic group or a $C_1$ methyl substituted group.

The one or more substituted or unsubstituted amino acids may be any essential or non-essential naturally occurring amino acids or non-naturally occurring amino acids. Preferred amino acids are alanine, β-alanine and glycine.

The substituents of the mass normalisation moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary, and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

Enrichment of Labelled Peptides

It is preferred that the first, second, third, fourth and fifth aspects of the invention may additionally incorporate a means for the selective enrichment of labelled peptides prior to analysis by mass spectrometry. The particular method used for such enrichment is not particularly limiting and many such methods are well known in the art including incorporation of an affinity capture ligand. Affinity capture ligands are ligands which have highly specific binding partners. These binding partners allow molecules tagged with the ligand to be selectively captured by the binding partner. Preferably a solid support is derivatised with the binding partner so that affinity ligand tagged molecules can be selectively captured onto the solid phase support. A preferred affinity capture ligand is biotin, which can be introduced into the mass labels of this invention by standard methods known in the art. In particular a lysine residue may be incorporated after the mass marker moiety or mass normalization moiety through which an amine-reactive biotin can be linked to the mass labels (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analogue of [Lys]bradykinin." 1991; Natarajan S. et al., Int J Pept Protein Res 40(6): 567-567, "Site-specific biotinylation. A novel approach and its application to endothelin-1 analogues and PTH-analogue.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture mass labels. As a further alternative, an affinity capture functionality may be selectively reactive with an appropriately derivatised solid phase support. Boronic acid, for example, is known to selectively react with vicinal cis-diols and chemically similar ligands, such as salicylhydroxamic acid.

Biological Molecules

The term biological molecule is not especially limiting and includes proteins, glycoproteins, peptides, polypeptides, amino acids, nucleic acids, hormones, metabolites, and carbohydrates. Steroids are an important class of hormones. Examples of steroid hormones include estrogens, progesterone and testosterone. The accurate analysis and quantification of hormones in body liquids such as plasma, serum, urine or saliva is becoming more important. For example, estrogen and estrogen like compounds are playing an important role in hormone replacement therapy. Also, the analysis and quantification of estrogen and estrogenic compounds helps in the management of estrogen-related diseases, like breast cancer.

Sets of Mass Labels

In another aspect the invention provides a set of two or more reactive mass labels, wherein each label in the set is as defined above and wherein each mass normalisation moiety ensures that a mass label has a desired aggregate mass, and wherein the set comprises:

a group of labels having a mass marker moiety of common mass, each label in the group having a unique aggregate mass; or a group of labels having a mass marker moiety, each mass marker moiety having a mass different from that of all other mass marker moieties in that group, and each label in the group having a common aggregate mass;

and wherein all the mass labels in the set are distinguishable from each other by mass spectroscopy.

In one embodiment, each label in the set comprises a mass marker moiety having a common mass and each label in the set has a unique aggregate mass (the first label type). In another embodiment, each label in the set comprises a mass marker moiety having a unique mass and each label in the set has a common aggregate mass (the second label type).

The set of labels need not be limited to the two preferred embodiments described above, and may for example comprise labels of both types, provided that all labels are distinguishable by mass spectrometry.

It is preferred that, in a set of labels of the second type, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or more moieties share a structure which has substantially the same structural skeleton, backbone or core. The skeleton comprises the mass marker moiety of the formula given above or the mass normalisation moiety as defined above, but may additionally comprise a number of amino acids linked by amide bonds. However, other units such as aryl ether units may also be present. The skeleton or backbone may comprise substituents pendent from it, or atomic or isotopic replacements within it, without changing the common basic structure.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety and any other components of the mass label.

The mass normalisation moiety is only limited by its mass, which may vary between different mass labels in a set. For instance, where a set comprises a group of labels having mass marker moieties of different masses but a common aggregate mass, the mass of the mass normalisation moiety will be different in each mass label in the set. In this case, the mass of the mass normalisation moiety in each individual mass label will be equal to the common aggregate mass minus the mass of the particular mass marker moiety in that mass label and minus the mass of the cleavable linker. Where the set comprises a group of labels having a mass marker moiety of common mass but different aggregate masses, it is clear that the mass of the mass normalisation moiety will need to vary such that the aggregate mass of all labels in the group is different.

All mass labels in the set are distinguishable from each other by mass spectroscopy. Therefore, a mass spectrometer can discriminate between the mass labels, i.e. the peaks derived from individual mass labels can be clearly separated from one another. The difference in mass between the mass marker moieties or the mass labels means that a mass spectrometer can discriminate between ions derived from different mass labels or mass marker moieties.

Preferably, each mass label in the set comprises A which has the following structure:

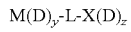

wherein M is a mass normalisation moiety, X is a mass marker moiety, D is a mass adjuster moiety, L is a cleavable linker, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group.

If the set of mass labels is of the second type referred to above the sum of the masses of M and X is the same for all members of the set. Preferably M and X have the same basic structure or core structure, this structure being modified by the mass adjuster moieties. The mass adjuster moiety ensures that the sum of the masses of M and X in is the same for all mass labels in a set, but ensures that each X has a distinct (unique) mass.

The mass adjuster moiety is preferably selected from:
(a) an isotopic substituent situated within the mass marker moiety and/or within the mass normalisation moiety, and
(b) substituent atoms or groups attached to the mass marker moiety and/or attached to the mass normalisation moiety.

Typically the mass adjuster moiety is selected from a halogen atom substituent, a methyl group substituent, and $^2$H, $^{15}$N, $^{13}$C or $^{18}$O isotopic substituents.

In one preferred embodiment of the invention, each mass label in the set comprises A which has the following structure:

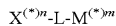

wherein X is the mass marker moiety, L is the cleavable linker and M is the mass normalisation moiety, and * is an isotopic mass adjuster moiety, and n and m are integers of 0 or greater such that either:
each label in the set comprises a mass marker moiety having a common mass and each label in the set has a unique aggregate mass; or
each label in the set comprises a mass marker moiety having a unique mass and each label in the set has a common aggregate mass.

It is preferred that X comprises the following group:

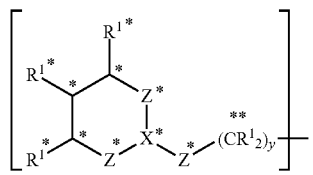

wherein $R^1$, Z, X and y are as defined above and each label in the set comprises 0, 1 or more * such that either:
each label in the set comprises a mass marker moiety having a common mass and each label in the set has a unique aggregate mass; or
each label in the set comprises a mass marker moiety having a unique mass and each label in the set has a common aggregate mass.

In a preferred embodiment the mass marker moiety comprises a group selected from the following groups:

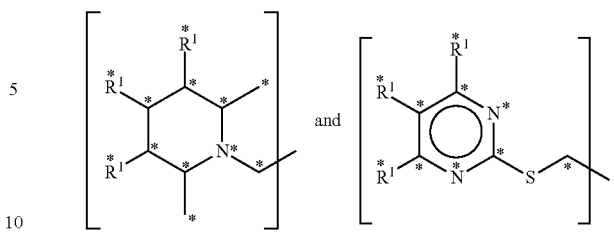

wherein the set comprises 0, 1 or more * such that either:
each label in the set comprises a mass marker moiety having a common mass and each label in the set has a unique aggregate mass; or
each label in the set comprises a mass marker moiety having a unique mass and each label in the set has a common aggregate mass.

In a further preferred embodiment the mass marker moiety comprises a group selected from the following groups:

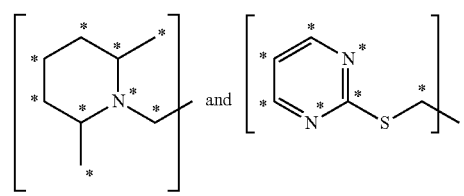

wherein the set comprises 0, 1 or more * such that either:
each label in the set comprises a mass marker moiety having a common mass and each label in the set has a unique aggregate mass; or
each label in the set comprises a mass marker moiety having a unique mass and each label in the set has a common aggregate mass.

Preferably, the set of reactive mass labels comprises two or more mass labels of any of the following structures:

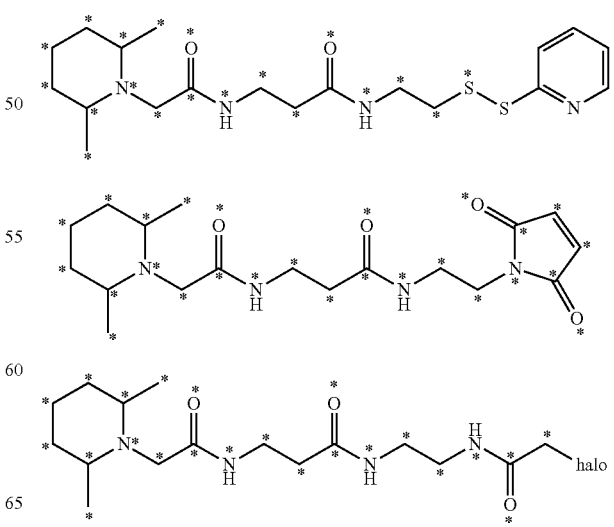

-continued

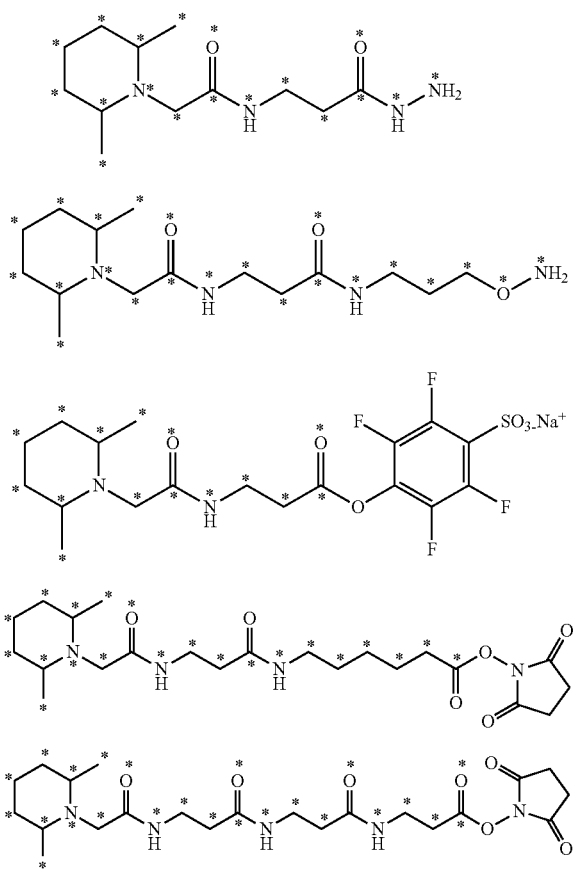

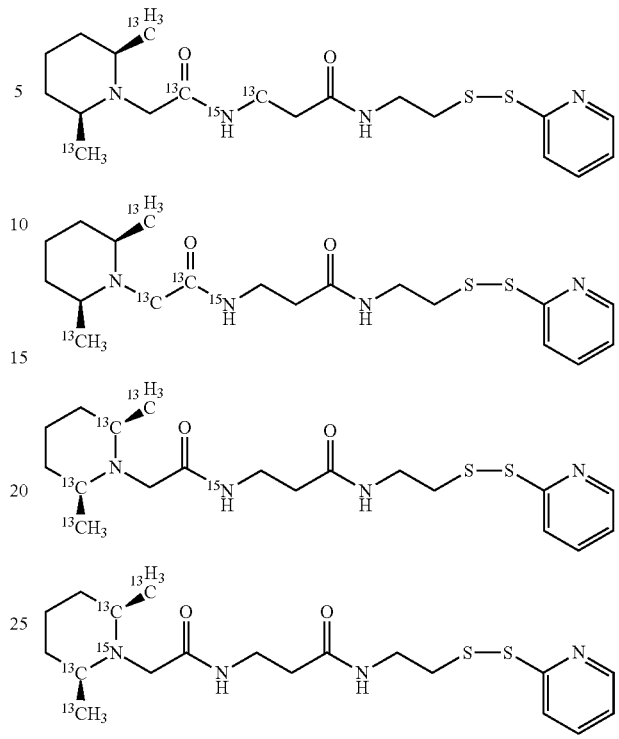

wherein * represents that the oxygen is $O^{18}$, carbon is $C^{13}$ or the nitrogen is $N^{15}$, and wherein the each label in the set comprises one or more * such that either:

each label in the set comprises a mass marker moiety having a common mass and each label in the set has a unique aggregate mass; or each label in the set comprises a mass marker moiety having a unique mass and each label in the set has a common aggregate mass.

In a particularly preferred embodiment, the mass adjuster moiety * is $C^{13}$ or $N^{15}$ and the set comprises six reactive mass labels having the following structures:

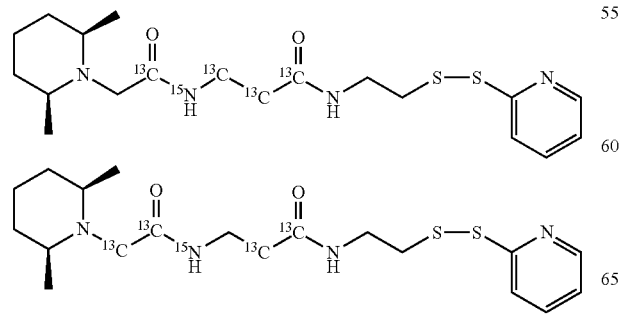

In another preferred embodiment the mass adjuster moiety * is $C^{13}$ or $N^{15}$ and the set comprises six reactive mass labels having the following structures:

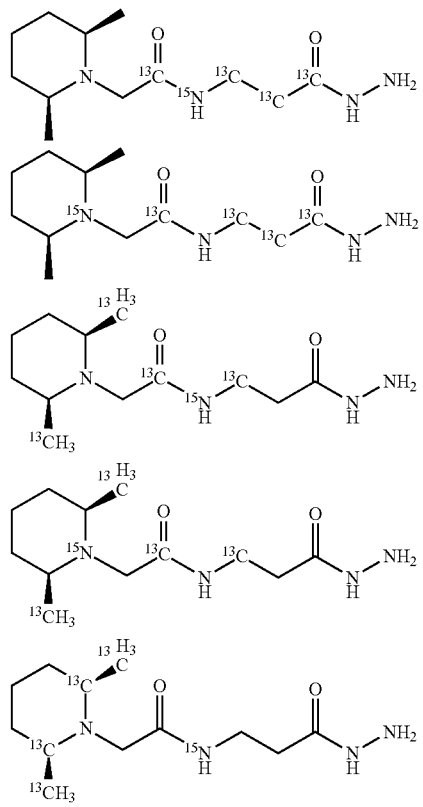

-continued

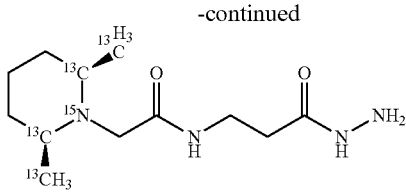

Alternatively, the mass adjuster moiety * is $C^{13}$ or $N^{15}$ and the set comprises six reactive mass labels having the following structures:

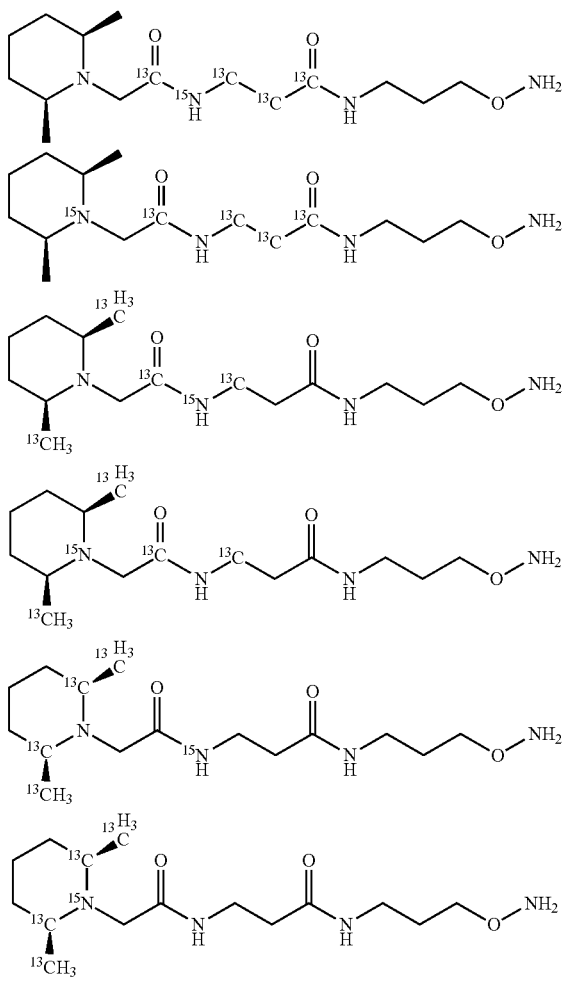

Arrays of Mass Labels

In a further aspect of the invention, provided is an array of mass labels, comprising two or more sets of mass labels as defined above, wherein the aggregate mass of each of the mass labels of any one set in the array is different from the aggregate mass of each of the mass labels of every other set in the array.

Preferably, each mass label in at least one set comprises a mass series modifying group of a common mass, the mass series modifying group in each of the mass labels of any one set having a different mass from the mass series modifying groups in each of the mass labels of every other set in the array.

Extended TMT Reagents to Achieve Increased Multiplex Capacity

The improvements in proteomic studies provided by isobaric mass tags with plexing rates up to six or eight has led to a desire to increase the multiplexing capacity of isobaric mass tags further. Whilst the current TMT core structure has the potential for a 9-plex set if all available atoms are substituted, the performance of the quantitation is likely to be negatively impacted by increasing the multiplex rates much above six in any set of isobaric reagents due to decreasing intensities of corresponding reporter ions. Above this level the precision of quantitation is likely to become less accurate with many proteins falling below the limit of detection. It is a further consideration that production costs of a single isobaric set of reagents with higher plexing rate will be prohibitive.

An alternative route to higher multiplex rates is to provide multiple sets of isobaric TMTsixplex reagents by addition of moieties which introduce different offset masses. U.S. Pat. No. 7,294,456 describes one approach to deliver an array of isobaric mass sets by linking the isobaric mass tags to a mass series modifying group. The examples provided in U.S. Pat. No. 7,294,456 use different levels of substitution with fluorine or methyl groups, or different numbers of cyclic aryl ethers. Whilst these approaches achieve the desired aim, there is a risk that the use of non-identical structures in the mass series modifying group will affect chromatographic retention time or the co-migration in 1- or 2-dimensional gel electrophoresis.

To provide an improved means of manufacturing arrays of isobaric mass tag sets a series of isotopically doped mass series modifying groups have been developed. In addition, a method of synthesis of adding the mass series modifying groups to existing mass labels was used to simplify synthesis of multiple sets and retains the same core structure and reporter species (mass marker moiety) which are known to reside in the silent region of the MS/MS spectra of peptides.

The term silent region of a mass spectrum (such as an MS/MS spectrum) used in the present context is intended to refer to the region of a mass spectrum with low background "noise" caused by peaks relating to the presence of fragments generated by fragmentation of the labelled peptides. An MS/MS spectrum is obtained by the fragmentation of one peak in MS-mode, such that no contaminants, such as buffering reagents, denaturants and detergent should appear in the MS/MS spectrum. In this way, quantification in MS/MS mode is advantageous. Thus, the term silent region is intended to refer to the region of the mass spectrum with low "noise" caused by peaks relating to the biological molecule to be detected. When the biological molecule to be detected is a peptide or protein, the silent region of the mass spectrum is less than 200 Daltons. When the biological molecule to be detected is DNA, RNA, an oligonucleotide or a nucleic acid base, the silent region of the mass spectrum is less than 500 Daltons.

Using this approach it is possible that two, three, four or even five TMTsixplex sets having six, twelve, eighteen, twenty-four and thirty individual mass tags respectively can be generated which are structurally identical but differ in mass. Such sets have isotopic and isobaric features combined in the same reagent, thereby increasing the multiplex capacity.

The nature of the mass series modifying group is not particularly limiting so long as it has a minimum of four atoms that can be substituted by heavy isotope atoms. It is preferred that the mass series modifying group has a free amine group to allow facile coupling to the existing TMT core molecule. It is further preferred that the mass series modifying group additionally has a reactive group that is able to react with functional groups in proteins, nucleic acids, lipids or sugars.

Alternatively the mass series modifying group may be readily derivatised to provide such reactivity.

The TMT core structure preferably contains a βAlanine residue as the mass normalisation group. This contains a free carboxyl acid moiety that can readily be reacted with a free-amine containing mass series modifying reagent.

The present invention provides a reactive mass label for labelling a biological molecule for detection by mass spectrometry, wherein the mass label comprises the following structure:

wherein X is a mass marker moiety, L is a cleavable linker, M is a mass normalization moiety, S is a mass series modifying group comprising the following group:

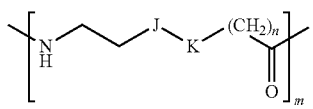

wherein J is C=O, K is NH, and n is 2 or J and K are both CH$_2$ and n is 1, and wherein m is at least 1; and
Re is a reactive functionality for attaching the mass label to a biological molecule.
m may be from 1 to 10, preferably from 1 to 5, more preferably 1 or 2, most preferably 1.

Thus, the mass series modifying group preferably comprises:

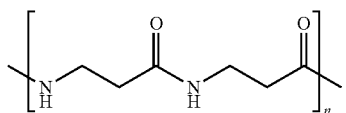

or:

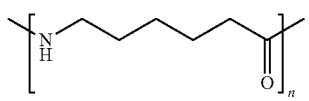

wherein n is at least 1.
n may be from 1 to 10, preferably from 1 to 5, more preferably 1 or 2, most preferably 1.

It will be understood that the mass series modifying group can be incorporated into mass labels comprising any reactive functionality, including amine reactive, cysteine reactive and carbonyl reactive functionalities. Preferably, the reactive functionality is as defined in any of a) to d) above.

In another preferred embodiment the reactive functionality comprises the following group:

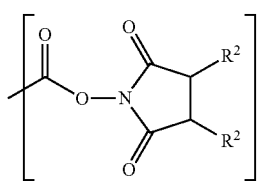

wherein each R$^2$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group. This reactive group is designed to react with amine groups of biomolecules.

In a preferred array, each mass label in at least one set comprises a mass series modifying group comprising the following group:

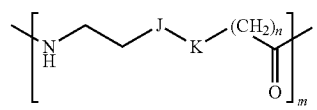

wherein J is C=O, K is NH, and n is 2 or J and K are both CH$_2$ and n is 1, and wherein m is at least 1; and the mass series modifying group of each of the mass labels of any one set has a different mass from the mass series modifying groups in each of the mass labels of every other set in the array due to the presence of a different number of isotopic mass adjuster moieties *.

In a preferred embodiment a βAla-βAla dipeptidyl mass series modifying group has been prepared into which various levels of heavy isotope atoms can be exchanged. In another embodiment an aminohexanoic acid mass series modifying group has been prepared into which various levels of heavy isotope atoms can be exchanged.

Thus, the mass series modifying group preferably comprises:

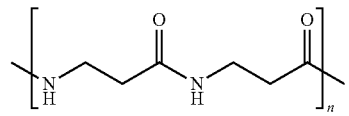

or:

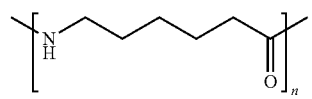

wherein n is at least 1, and the mass series modifying group of each of the mass labels of any one set has a different mass from the mass series modifying groups in each of the mass labels of every other set in the array due to the presence of a different number of isotopic mass adjuster moieties *.

In a particularly preferred embodiment the array of mass labels comprises:
a) a first set of mass labels, wherein each mass label in the set comprises a mass modifying group having the following structure:

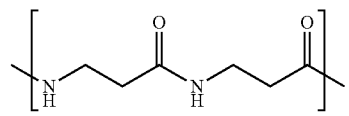

b) a second set of mass labels, wherein each mass label in the set comprises a mass modifying group having the following structure:

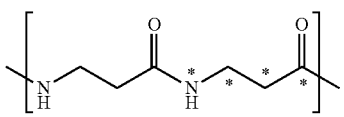

and;

c) a third set of mass labels, wherein each mass label in the set comprises a mass modifying group having the following structure:

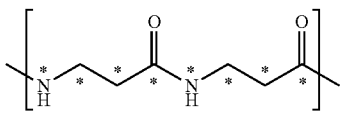

FIG. 11 shows an array of different label structures with light, medium (+4 Da) and heavy (+8 Da) relative masses. The βAla-βAla dipeptidyl mass series modifying group is highlighted in FIG. 11. FIG. 12 shows the synthetic strategy for the different members of the array. Individual syntheses require starting forms of DMP-bALA and bALA building blocks carrying different levels of isotope substitution. To form an array of sets of isobaric mass tags the DMP-βALA group carries the normal TMTduplex or TMTsixplex substitutions as disclosed in WO 2007/012849. By this method a 4-, 6-, 12- or 18-plex array is formed. It will be understood by the skilled practitioner that alternate isotopic substitutions can be incorporated to yield different offset masses and/or plexing rates.

Whilst the use of multiple βAlanines provides a relatively facile route to producing arrays of isobaric mass tags, it involves introducing additional cleavable amide bonds into the tag. These will fragment in the mass spectrometer and produce additional ions in the MS/MS spectrum. Whilst this may not be particularly disadvantageous for many applications, it may be desirable to avoid such additional fragments. One alternate approach is to use a single long chain amino acid such as aminohexanoic acid. Aminohexanoic acid has nine atoms that could be substituted with a stable heavy isotope equivalent offering mass differences of up to 10 Da. To demonstrate this aspect of the invention, a pair of isotopic TMT's using the core DMP-βALA extended with either light or heavy forms of aminohexanoic acid were synthesized. FIG. 13 shows two possible structures and indicates the atoms in the aminohexanoic acid carrying a heavy isotope substitution to deliver the desired offset mass. FIG. 14 shows a method of synthesizing the aminohexanoic acid mass labels.

Labelled Biological Molecules

The present invention provides mass labelled biological molecules. The invention also provides sets and arrays of mass labelled biological molecules.

In one embodiment, each biological molecule is preferably attached to a unique combination of mass labels, each combination being distinguished by the presence or absence of each mass label in the set of mass labels and/or the quantity of each mass label attached to the biological molecule. As mentioned above, this is termed the "mixing mode" of the present invention, since the biological molecules may be attached to a mixture of mass labels.

Analysis of Peptides by Mass Spectrometry

The essential features of a mass spectrometer are as follows:

Inlet System→Ion Source→Mass Analyser→Ion Detector→Data Capture System

There are preferred inlet systems, ion sources and mass analysers for the purposes of analysing peptides.

Inlet Systems

In some aspects of this invention a chromatographic or electrophoretic separation is preferred to reduce the complexity of the sample prior to analysis by mass spectrometry. A variety of mass spectrometry techniques are compatible with separation technologies particularly capillary zone electrophoresis and High Performance Liquid Chromatography (HPLC). The choice of ionisation source is limited to some extent if a separation is required as ionisation techniques such as MALDI and FAB (discussed below) which ablate material from a solid surface are less suited to chromatographic separations. For most purposes, it has been very costly to link a chromatographic separation in-line with mass spectrometric analysis by one of these techniques. Dynamic FAB and ionisation techniques based on spraying such as electrospray, thermospray and APCI are all readily compatible with in-line chromatographic separations and equipment to perform such liquid chromatography mass spectrometry analysis is commercially available.

Ionisation Techniques

For many biological mass spectrometry applications so called 'soft' ionisation techniques are used. These allow large molecules such as proteins and nucleic acids to be ionised essentially intact. The liquid phase techniques allow large biological molecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation

Electrospray ionisation requires that the dilute solution of the analyte biological molecule is 'atomised' into the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biological molecules have a net charge this increases the electrostatic repulsion of the dissolved molecule. As evaporation continues this repulsion ultimately becomes greater than the surface tension of the droplet and the droplet disintegrates into smaller droplets. This process is sometimes referred to as a 'Coulombic explosion'. The electrostatic field helps to further overcome the surface tension of the droplets and assists in the spraying process. The evaporation continues from the smaller droplets which, in turn, explode iteratively until essentially the biological molecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labelled biological molecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI)

MALDI requires that the biological molecule solution be embedded in a large molar excess of a photo-excitable 'matrix'. The application of laser light of the appropriate frequency results in the excitation of the matrix which in turn leads to rapid evaporation of the matrix along with its entrapped biological molecule. Proton transfer from the acidic matrix to the biological molecule gives rise to protonated forms of the biological molecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation with this technique though.

Fast Atom Bombardment

Fast Atom Bombardment (FAB) has come to describe a number of techniques for vaporising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the fit surface by atom bombardment.

Mass Analysers

Fragmentation of peptides by collision induced dissociation is used in this invention to identify tags on proteins. Various mass analyser geometries may be used to fragment peptides and to determine the mass of the fragments.

MS/MS and MS Analysis of Peptides

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

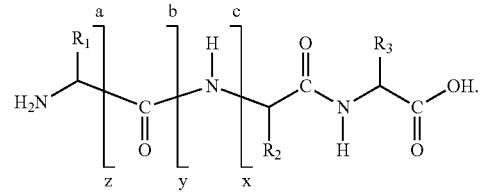

Trypsin and thrombin are favoured cleavage agents for tandem mass spectrometry as they produce peptides with basic groups at both ends of the molecule, i.e. the alpha-amino-group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. D. J. Mass Spectrom. 35: 1382-1390, "Five-membered ring formation in unimolecular reactions of peptides: a key structural element controlling low-energy collision induced dissociation", 2000).

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem analysers. Ion trap mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions. Another favourable geometry is a Quadrupole/Orthogonal Time of Flight tandem instrument where the high scanning rate of a quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Traps

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Separation of Labelled Peptides by Chromatography or Electrophoresis

In a preferred embodiment of the invention labelled biomolecules are subjected to a chromatographic separation prior to analysis by mass spectrometry. This is preferably High Performance Liquid Chromatography (HPLC) which can be coupled directly to a mass spectrometer for in-line analysis of the peptides as they elute from the chromatographic column. A variety of separation techniques may be performed by HPLC but reverse phase chromatography is a popular method for the separation of peptides prior to mass spectrometry. Capillary zone electrophoresis is another separation method that may be coupled directly to a mass spectrometer for automatic analysis of eluting samples. These and other fractionation techniques may be applied to reduce the complexity of a mixture of biological molecules prior to analysis by mass spectrometry. A combination of separation techniques may also be used, including orthogonal separation.

Methods of Analysis

A further aspect of the invention is provided by use of a reactive mass label as defined above in a method of analysis by mass spectrometry.

Also provided is a method of analysis, which method comprises detecting a biological molecule by identifying by mass spectrometry a mass label relatable to the biological molecule, wherein the mass label is a mass label as defined above.

Preferably, the method comprises the following steps:
1. reacting the biological molecule with a reactive mass label as defined above;
2. separating the labelled biological molecule;
3. identifying by mass spectrometry the mass label relatable to the biological molecule.

Preferably the mass spectrometry is tandem mass spectrometry. In a particularly preferred embodiment the invention step 2. comprises separating the unlabelled analytes from the labelled analytes by reverse phase high pressure liquid chromatography, cation exchange or size exclusion chromatography.

EXAMPLES

Example 1

Figure 2:
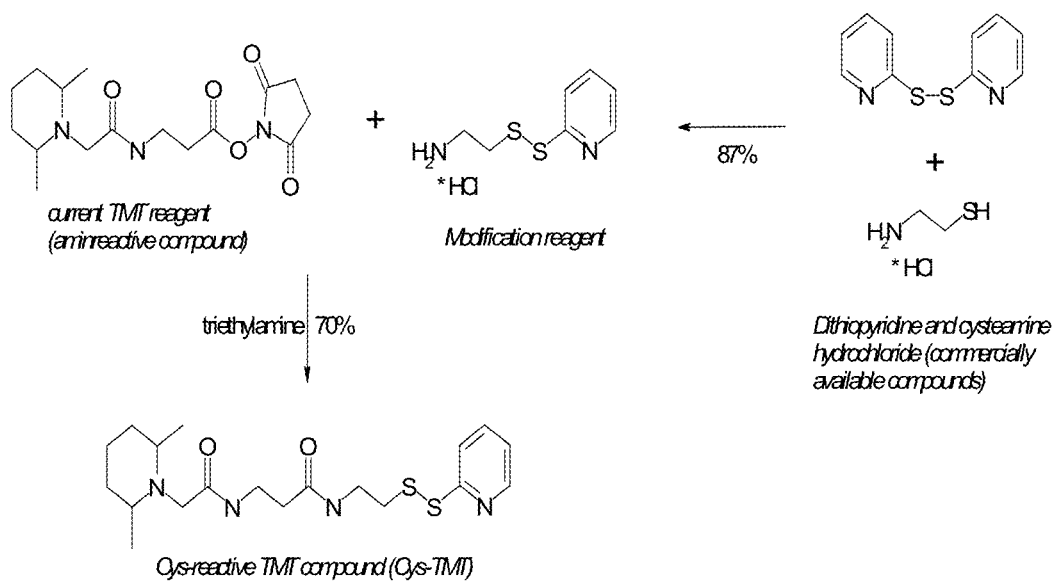
FIG. 2 shows a reaction scheme for the synthesis of a cysteine reactive mass label, DMPip-βALA-DTP, with obtained yields. Starting point are the established TMT structure and commercially available compounds.

Synthesis of Dimethylpiperidine-βAlanine-Dithiopyridine: A Cysteine-Reactive Mass Label It is a convenient feature of the DMPip-βALA-OSu structure that alternate reactivities can be readily created by reaction with the succinimide ester reactive group. Thus, using the known TMT (Tandem Mass Tag or mass label) structure previously disclosed in WO2007/012849 as a starting point and commonly available building blocks, a reaction scheme was designed which requires only one more reaction step to convert the amino-reactive compound into the respective cysteine-reactive compound. We first synthesised the dithiopyridine modification reagent from commercially available compounds in a single reaction with good yield. This reagent was then allowed to react with DMPip-βALA-OSu to generate the DMPip-βALA-DTP reagent (see FIG. 2). Analysis by HPLC, MS and MS/MS revealed the correct identity and a purity >90%.

Example 2

Labelling of Synthetic Peptides Using DMPip-βAla-DTP

The quality controlled DMPip-βALA-DTP reagent was then applied to develop a labelling protocol. An individual cysteine-containing peptide (H-Vat-Ala-Thr-Val-Cys-Leu-Pro-Arg-OH) was chosen to allow for an easy monitoring of the reaction progress by HPLC with UV-readout. A protocol was developed that yields an essentially complete labelling. 50 µg BSA were dissolved in 100 µL TEAB (100 mM, pH 8.5) including 0.1% SDS. After reduction with 1 mM of tris[2-carboxyethyl]phosphine * HCl for 1 h at 55° C., the Cys residue was labelled with 5 mM DMPip-βALA-DTP (provided as 200 mM stock solution in methanol). Purification of the reaction mixture using RP and SCX cartridges obtained modified peptide in a highly purified form. FIG. 3 shows HPLC monitoring of the individual species in the labelling reaction.

Example 3

Synthesis of Mass Labels for Steroid Analysis

The analysis of hormones is typically performed by radioimmunoassay and colorimetric or chemiluminscent enzyme immunoassay. However, current immunoassays are disadvantageous since they are limited to quantitative detection of only one steroid hormone per assay, may lack specificity, and as a result of such cross-reactivity can show up to 15 fold variance in the quantitative results of the same sample when using kits from different manufacturers.

An alternate approach for measurement of steroids is gas chromatography-mass spectrometry (GC-MS). GC-MS is both sensitive and specific, but requires tedious and time-consuming sample preparation. Liquid chromatography-MS (LC-MS) and liquid chromatography-tandem MS are equally specific and offer simpler approaches to sample preparation often without such complex sample derivatization steps. Recently, a number of LC-MS-based methods using different ion sources have been reported for the determination of steroid hormones. Stable isotope dilution tandem MS in the multiple reaction monitoring mode (MRM) allows for the rapid simultaneous quantitation of numerous steroids in a single sample. Typically for such assays steroids are derivatized into Girard P hydrazones at their carbonyl functions and can be identified by tandem MS with high sensitivity at the sub-picogram level. Whilst the derivatisation of steroids at the carbonyl group is particularly desirable, other derivatisations on the hydroxyl groups may also be used such as derivatization to picolinyl or dimethylglycine esters. Irrespective of the derivatisation used this method is especially useful for the quantitation of neutral steroids.

Whilst LC-MS/MS methods have provided some advantages over immunoassays and GC-MS analysis, they are still limited in being able to analyse only one sample at a time. It is desirable to provide alternate derivatization reagents to allow the analysis of multiple steroids in multiple samples simultaneously. Alternatively it would be particularly desirable to allow derivatisation of steroids from several samples and reference standards using mass tags that then allow for the mixing and combined analysis of all samples in a single assay. Currently known TMT reagents offer such mixing capabilities but lack the necessary reactive group for labelling of steroids via carbonyl or hydroxyl groups.

To provide improved reagents for the analysis of steroid hormones by LC-MS/MS new isobaric tandem mass tags with carbonyl reactivity were prepared.

In a first approach the free acid form of the dimethylpiperidine-βalanine-OSu TMT core molecule was activated with di-(N,N'-succinimidyl) carbonate (DSC) and reacted with hydrazine to form the dimethylpiperidine-βalanine-hydrazide tag.

In a second approach dimethylpiperidine-βalanine as free acid was activated with DSC and reacted with Boc-protected aminoxypropylamine to form an aminoxypropyl reactive group. Using these tags Steroids are derivatized to yield hydrazones or O-alkyloximes, respectively. These are quantified by LC-tandem MS. The use of the TMT tags provides several advantages over current analytical methods. By introducing a basic moiety the ionization and sensitivity even of neutral steroids in LC-MS is improved. The tags will react with all steroids bearing carbonyl groups and so numerous steroids can be analysed in a single sample. In their isobaric form these reagents allow the simultaneous quantitation and comparison of several samples in one experiment.

The synthesis reactions for the hydrazide and aminoxypropyl TMT reagents are shown in FIGS. 5 and 6.

Example 4

Labelling of Steroids with DMPip-βAla-Hydrazide

Three steroids testosterone, nandrolone and betamethasone were labelled with non-isotopically doped DMPip-βAla-hydrazide and subjected to LC-MS/MS analysis. Briefly 10 mg of the three steroid mixture was dissolved in 1 mL $C_2H_5OH/CH_3CO_2H/H_2O$ (7:1:2). To this was added 10 mg of DMPip-βAla-hydrazide and the mixture heated at 70° C. for 30 mins. After labelling was complete the mixture was cleaned by passing through a Sep-PAK $C_{18}$ column prior to analysis by LC-MS/MS on an LTQ-Orbitrap (Thermo Scientific). FIG. 7 shows the MS profile of the derivatised steroid mix with peaks for testosterone (T+H), Nandrolone (N+H) and Betamethasone (B+H) clearly shown.

When each of these ions was subjected to tandem mass spectrometry a set of unique fragments were produced allowing identification of the steroid. In addition, a unique DMPip-βAla-hydrazide tag-derived ion with m/z of 126.1 Da was produced. This fragment is the mass reporter group (mass marker moiety) of the core TMT mass label molecule and is used in quantitation of the identified steroid. When a series of isobaric DMPip-βAla-hydrazide tags are used it is possible to label several steroid containing samples and then mix them for subsequent analysis. In this case the abundance of the TMT-derived reporter ions provides the quantitation for the identified steroid in each respective sample. FIG. 8 shows the MS/MS profile for Nandrolone and Testosterone.

Example 5

Performance of Exemplar TMT Array Reagents

Both the βAlanine and aminohexanoic acid extended reagents were found to have very similar performance to the standard TMT reagent in terms of solubility in organic and organic-aqueous solvents and labelling efficiency. Thus, the labelling protocol as used for the standard TMT reagents was kept and used to label a tryptic digest of bovine serum albumin (BSA). These samples were purified and subjected to LC-MS/MS analyses.

Data Obtained with the TMT Reagent Extended by Two βAlanine Moieties

Despite the increase in the mass of the TMT array tags due to additional βAla groups the elution of individual peptides was not found to be significantly altered when labelled with the new TMT reagents compared to the standard TMT, the observed shift is less than 1 min. Also the MS/MS behaviour was found to be very similar to the standard reagent. FIG. 15A shows the total ion count chromatogram for a BSA tryptic digest labelled with either DMP-βALA-OSu or DMP-(βAla)3-OSu respectively. The respective ion for a chosen peptide and its corresponding MS/MS profile is shown in FIG. 15B. It can be seen that the fragment ions are essentially identical save for the mass shift induced by the tag, and that the confidence of identification in SEQUEST is not affected by additional tag-related fragments.

To further investigate the potential impact of additional tag fragment peaks on the MS/MS profile of individual peptides a detailed analysis of all MS/MS spectra from the tryptic digest of BSA was performed. Whilst further fragmentation at each additional amide bond could clearly be seen, this did not appear to influence the peptide identification scores and occurred in an entirely predictable way. If necessary the tag-derived fragment peaks could be excluded from database searches. FIG. 16 shows the MS/MS spectra of the mass label fragments for both the standard TMT reagent and the 2× beta-alanine extended one.

Data Obtained with the TMT Reagent Extended by Aminohexanoic Acid

Similar investigations were performed with the same tryptic digest of bovine serum albumin but labelled with the TMT reagent extended by an aminohexanoic acid residue. In this case, a significant shift of up to five minutes longer retention time was observed compared to the standard TMT reagent. The other investigated features (general MS and MS/MS behaviour, efficiency of search algorithms, additional fragments) are very similar to the DMPip-(βAla)3-OSu reagent and followed expected behaviour.

Example 6

Synthesis of a Mass Label with a Sulfo-Tetrofluorophenyl Reactive Group

The synthesis of the label is a one step reaction, wherein the starting point is the corresponding acid:

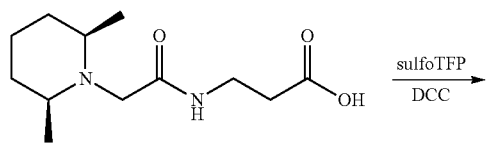

-continued

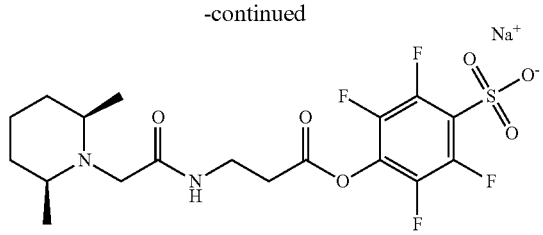

The invention claimed is:

1. A set of two or more reactive mass labels, wherein each reactive mass label in the set is for labeling a biological molecule for detection by mass spectrometry, each reactive mass label comprising the following structure:

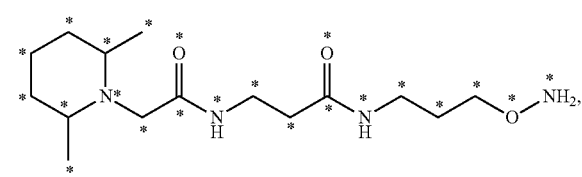

wherein

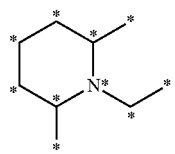

is the mass marker moiety, and wherein * is a mass adjuster moiety selected from the group consisting of $^{18}O$, $^{13}C$, and $^{15}N$, and wherein each reactive mass label in the set comprises one or more * such that either:

(a) the mass marker moiety of each reactive mass label in the set has a common mass and each reactive mass label in the set has a unique aggregate mass, and wherein all the reactive mass labels in the set are distinguishable from each other by mass spectroscopy; or (b) the mass marker moiety of each reactive mass label in the set has a unique mass and each reactive mass label in the set has a common aggregate mass, and wherein all the reactive mass labels in the set are distinguishable from each other by mass spectroscopy.

2. The set of two or more reactive mass labels according to claim 1, in which the mass marker moiety of each reactive mass label in the set has a common mass and each reactive mass label in the set has a unique aggregate mass.

3. The set of two or more reactive mass labels according to claim 1, in which the mass marker moiety of each reactive mass label in the set has a unique mass and each reactive mass label in the set has a common aggregate mass.

4. The set of reactive mass labels according to claim 1, wherein the mass adjuster moiety * is $^{13}C$ or $^{15}N$ and the set comprises six reactive mass labels having the following structures:

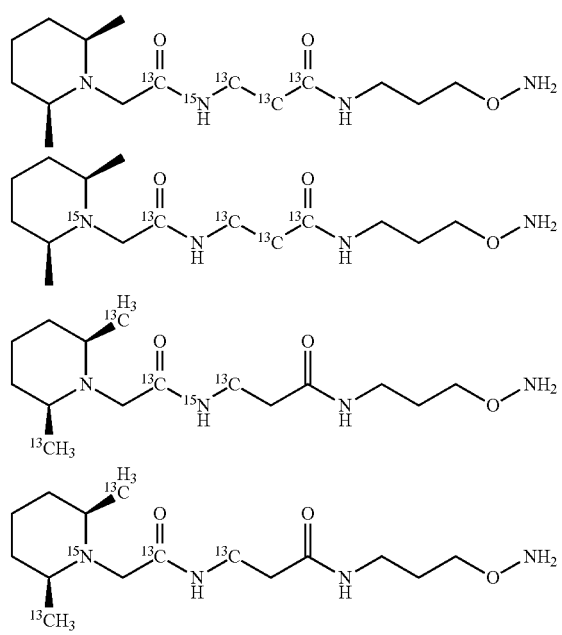
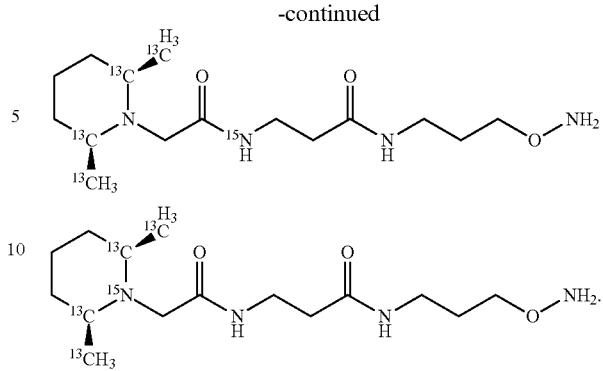
5. An array of reactive mass labels, comprising two or more sets of reactive mass labels as set forth in claim 1, wherein the aggregate mass of each of the reactive mass labels of any one set in the array is different from the aggregate mass of each of the reactive mass labels of every other set in the array.
\* \* \* \* \*